(12) United States Patent
Saini et al.

(10) Patent No.: US 9,386,954 B2
(45) Date of Patent: Jul. 12, 2016

(54) METHOD OF FABRICATING A MULTI-ELECTRODE ARRAY

(71) Applicant: Zyvex Labs, LLC, Richardson, TX (US)

(72) Inventors: Rahul Saini, Allen, TX (US); John Neal Randall, Richardson, TX (US)

(73) Assignee: Zyvex Labs, LLC, Richardson, TX (US)

( * ) Notice: Subject to any disclaimer, the term of this patent is extended or adjusted under 35 U.S.C. 154(b) by 452 days.

(21) Appl. No.: 13/833,037

(22) Filed: Mar. 15, 2013

(65) Prior Publication Data

US 2014/0275934 A1 Sep. 18, 2014

(51) Int. Cl.
| | |
|---|---|
| *A61N 1/04* | (2006.01) |
| *A61B 5/00* | (2006.01) |
| *A61N 1/05* | (2006.01) |
| *A61B 5/04* | (2006.01) |
| *A61B 5/0492* | (2006.01) |

(52) U.S. Cl.
CPC ........... *A61B 5/6846* (2013.01); *A61B 5/04001* (2013.01); *A61B 5/0492* (2013.01); *A61N 1/05* (2013.01); *A61N 1/0543* (2013.01); *Y10T 29/49117* (2015.01)

(58) Field of Classification Search
CPC ..... A61N 1/05; A61N 1/0543; H05K 3/0047; A61B 5/04001; A61B 5/0492; A61B 5/6846; Y10T 29/49117
See application file for complete search history.

(56) References Cited

U.S. PATENT DOCUMENTS

| | | | |
|---|---|---|---|
| 7,248,928 B2 | 7/2007 | Yagi | |
| 8,560,083 B2* | 10/2013 | Janik | A61N 1/0053 607/116 |
| 2001/0030330 A1 | 10/2001 | Inomoto | |
| 2007/0169333 A1 | 7/2007 | Donoghue et al. | |
| 2009/0293270 A1* | 12/2009 | Brindley | A61N 1/05 29/829 |
| 2011/0172736 A1 | 7/2011 | Gefen et al. | |

OTHER PUBLICATIONS

Patent Cooperation Treaty—International Searching Authority—United States, Notification of Transmittal of the International Search Report and the Written Opinion of the International Searching Authority, or the Declaration, mailed Jun. 23, 2014, Application No. PCT/US2014/023616, 10 pages, Alexandria, Virginia.

* cited by examiner

*Primary Examiner* — Carl Arbes
(74) *Attorney, Agent, or Firm* — Haynes and Boone, LLP

(57) ABSTRACT

A multi-electrode array with individually isolated electrodes each configurable for a target-containing carrier and a method for fabricating the array are disclosed. In an exemplary embodiment, the array includes a substrate; and a plurality of electrodes disposed on the substrate. Each electrode of the plurality of electrodes has a conductive tip-end and an insulated remainder. A first electrode of the plurality of electrodes has a first configuration selected to bring a conductive tip end of the first electrode in proximity to a first target structure, and a second electrode of the plurality of electrodes has a second configuration selected to bring a conductive tip end of the second electrode in proximity to a second target structure. The first configuration and the second configuration are different. A first contact of the plurality of contacts may be electrically coupled to the first electrode through the substrate.

20 Claims, 19 Drawing Sheets

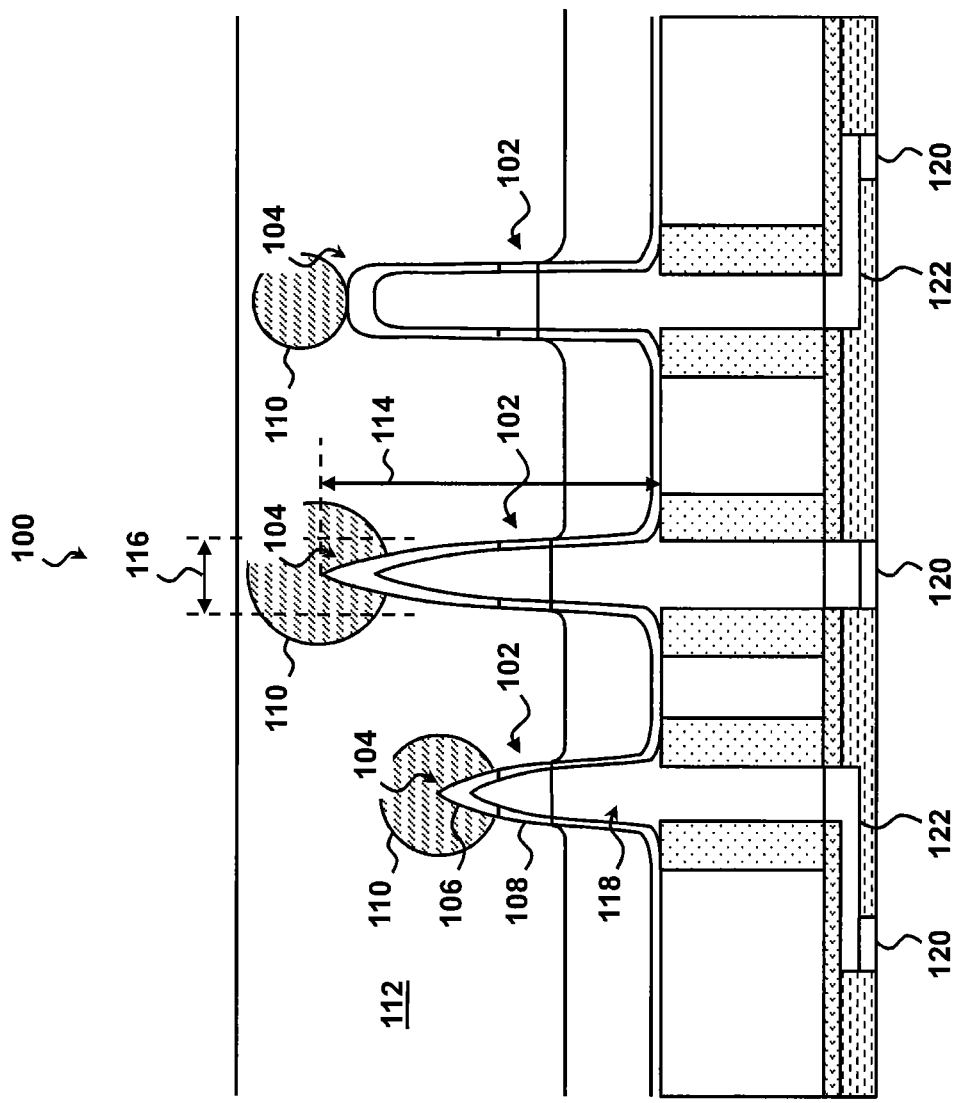

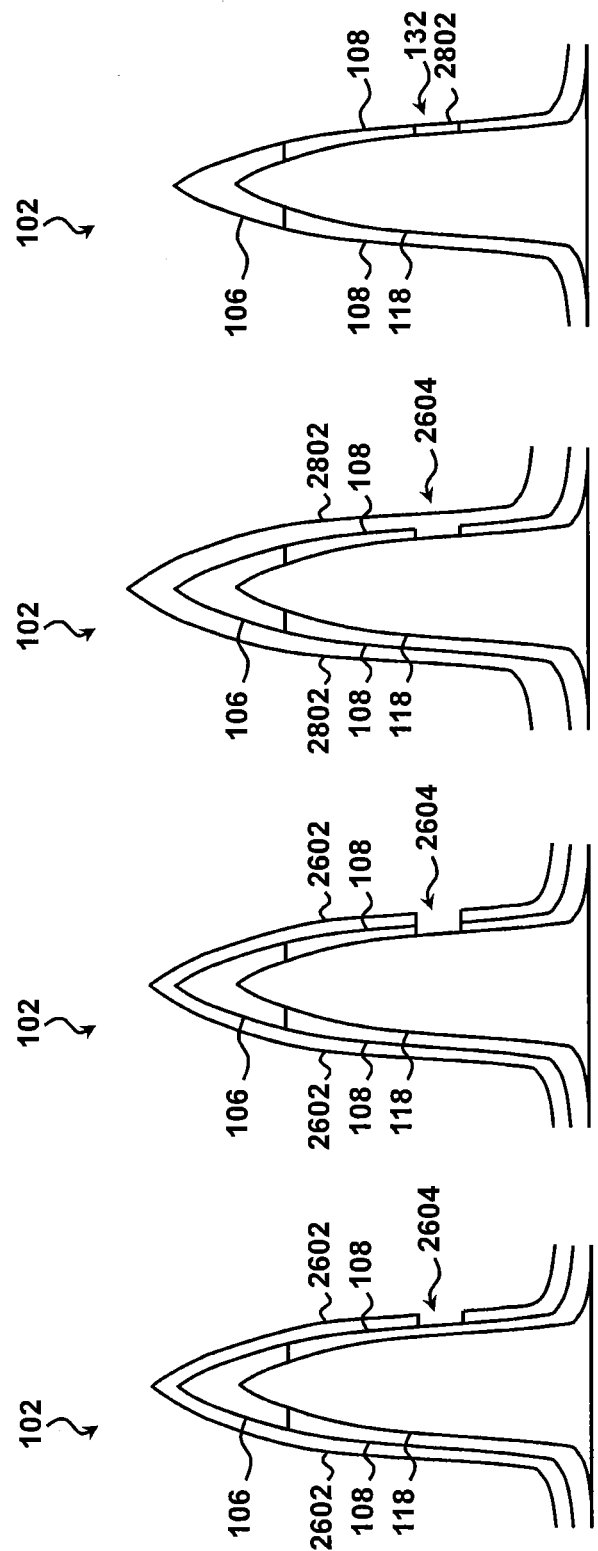

METHOD OF FABRICATING A MULTI-ELECTRODE ARRAY

TECHNICAL FIELD

The present disclosure relates to a three-dimensional, electrically isolated multi-electrode array (MEA) and to a method of forming the array. In some embodiments, the array comprises a plurality of electrodes of various heights and spacing aligned to contact with individual anatomical structures such as individual neurons within a cluster of neural tissue.

BACKGROUND

Advances in fabrication of increasingly miniscule integrated circuit (IC) devices have coincided with advances in the use of semiconductors to form mechanical and electromechanical structures. Generally referred to as microelectromechanical systems (MEMS), these minute devices are formed via fabrication procedures typically associated with integrated circuits and procedures unique to MEMS alone. MEMS development has given rise to miniature devices at sizes far below what was previously attainable and to entirely new devices altogether. MEMS devices are used in power generation, light projection, force sensing, switching, and locomotion to name merely a few examples, and have found applications in both the home and the laboratory.

One promising application of MEMS devices includes the use of nano-scale and micro-scale electrodes formed on an IC substrate to measure and stimulate living tissue. The MEMS electrodes may be used to provide electrical stimulation and to measure electrical activity. These electrical potentials may represent sensory perception, muscular control, and other neural signals, and the electrodes may provide an avenue to restore lost neural function by stimulating targeted neurons. However, the promised benefits have not yet been fully achieved. Key complications include providing localized measurement and electrically isolating the regions of interest. For these reasons and others, existing MEMS devices have been generally adequate but have not been entirely satisfactory in all respects.

BRIEF DESCRIPTION OF THE DRAWINGS

Illustrative embodiments of the present disclosure are described with reference to the accompanying drawings. It is emphasized that, in accordance with the standard practice in the industry, various features are not drawn to scale and are used for illustration purposes only. It is understood that the dimensions of the various features may be arbitrarily increased or reduced in the interest of clarity.

FIGS. 1A, 1B, 1C, and 1D are cross-sectional views of multi-electrode arrays (MEAs) according to various aspects of the present disclosure.

FIGS. 26-29 are diagrammatic cross-sectional views of an electrode undergoing a method for forming a conductive area along the body of the electrode according to various aspects of the present disclosure.

DETAILED DESCRIPTION

Figure 1D:
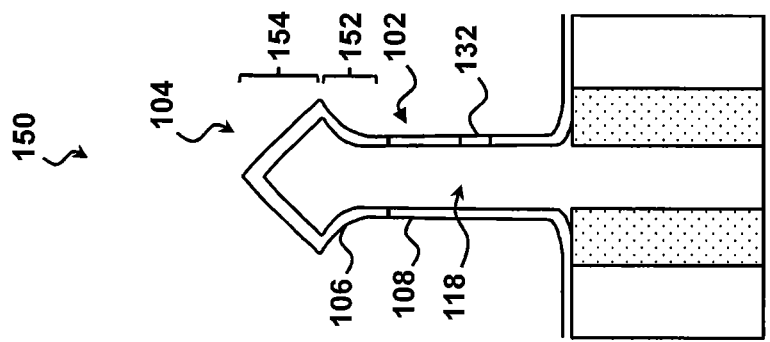

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described methods, devices, and systems, and any further application of the principles of the present disclosure are fully contemplated and included within the present disclosure as would normally occur to one of ordinary skill in the art to which the disclosure relates. In particular, it is fully contemplated that the steps, features, and/or components described with respect to one embodiment may be combined with the steps, features, and/or components described with respect to other embodiments of the present disclosure. For the sake of brevity, however, the numerous iterations of these combinations will not be described separately.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the device in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

FIG. 1A is a cross-sectional view of a multi-electrode array (MEA) 100 according to various aspects of the present disclosure. For clarity, only three electrodes 102 of the array 100 are illustrated. However, the array 100 may contain any suitable number of electrodes 102. In various exemplary embodiments, the array 100 includes between 1 and 20,000 electrodes 102 disposed in various patterns such as a linear M×N arrangement, a regular geometric pattern such as a parallelogram or other polygon, an irregular arrangement, and/or another suitable pattern. The electrodes 102 of the array 100 act as electrical conduits and may be used to measure electrical properties at the tip ends 104 of the electrodes and/or to deliver electrical stimulation. Accordingly, in some embodiments, the electrodes 102 are operable to measure electrical properties at the tip ends 104. In some embodiments, the electrodes 102 are operable to provide electrical stimulation at the tip ends 104. In yet further embodiments, the electrodes 102 are operable to measure electrical properties and to deliver electrical stimulation at the tip ends 104. Each electrode 102 may be electrically isolated from every other electrode 102 of the array.

The electrodes 102 are sized and structured to contact target structures 110 located in a carrier medium 112. In that regard, the target structures 110 may be any suitable electrical or electro-chemical structures, and may be distributed throughout any suitable carrier medium 112 including organic and inorganic carrier mediums. In some embodiments, the target-containing carrier 112 is a biological tissue such as retinal tissue, nervous tissue, cerebral tissue, muscle tissue, epithelial tissue, and/or other types of biological tissue known to one of ordinary skill in the art. For example, in an embodiment, the target structure 110 is a neural body located in a neural tissue carrier 112. In some embodiments, the carrier 112 includes multiple layers of varying type, such as epithelial tissue layers overlying muscle tissue layers. In further embodiments, the carrier 112 includes inorganic materials. It is understood that the present disclosure is not limited to any particular target structure 110 or carrier medium 112 and alternate target structures 110 and carrier mediums 112 are both contemplated and provided for.

To provide localized measurement and/or stimulation, the tip end 104 of each electrode 102 includes a conductive interface layer 106, while the remainder of the electrode 104 is insulated by a jacket layer 108. Thus, when the tip end 104 is placed in proximity to a target structure 110, the interface layer 106 provides a low-impedance electrical interface between the tip end of the electrode 102 and the target structure 110, while the jacket layer 108 inhibits electrical exchange between the body of the electrode 102 and adjacent structures. The jacket layer 108 may have a multi-layer composition, for example a silicon nitride inner layer with a silicon oxide outer layer. The inner layer or layers may provide support, may reduce strain, and/or have better gap fill properties than the outer layers, while the outer layer may have greater biocompatibility.

A conductive core 118 of the electrode electrically couples the tip end 104 of the electrode 102 to a contact or bonding pad 120 at the backside of the electrode 102. In some embodiments, the conductive core 118 is electrically conductive throughout. This provides an electrical connection between the target structure 110 and the bonding pad 120. A conductive trace 122 coupling the core 118 to the bonding pad 120 allows for configurations where the bonding pad 120 is directly aligned with the core 118 as well as configurations where the bonding pad 120 and the conductive core 118 are offset. In various embodiments, the bonding pads 120 are used to interface the electrodes 102 of the array 100 with an integrated circuit such as an ASIC, FPGA, DSP, microcontroller, CPU, system on a chip (SOC), and/or other computing device. This allows the integrated circuit to take sensor measurements and/or to deliver targeted stimulation at the tip end 104. In an exemplary embodiment, the electrodes 102 of the array 100 are introduced into a neural tissue carrier 112. A computing device coupled to the array 100 utilizes the electrodes 102 to measure and monitor neuro-electrical activity within the tissue. The computing device also utilizes the electrodes 102 to provide targeted electrical stimulation to regions of the neural tissue, particularly the regions in proximity to the tip ends 104 of the electrodes 102.

Each of the electrodes 102 of the array 100 may be individually configured based on a property of the associated target structure 110, a property of the carrier medium 112, a property of the electrode 102 function, and other considerations. This may include tailoring both physical and electrical properties of the electrodes 102. The following examples of electrode 102 configurations are provided to clarify the concepts of the present disclosure and are not intended to be limiting. Because the target structures 110 may vary in size and shape and may be distributed throughout the carrier medium 112, aspects of the electrodes 102 including height 114, width 116, amount of the electrode 102 covered by the conductive interface layer 106, electrode shape, spacing between electrodes 102, and/or other electrode characteristics may be configured to bring a tip end 104 in proximity to a particular target structure 110. In one such embodiment, the height 114 of an electrode 102 directly corresponds to a depth of the target structure 110 in the carrier medium 112. In a further exemplary embodiment, a spacing between electrodes corresponds to a spacing between target structures 110. In another exemplary embodiment, a width 116 corresponds to a size of a target structure 110.

As one skilled in the art will recognize, the carrier medium 112 may not be uniform. In many embodiments, the intended carrier medium 112 contains multiple layers or stratum, each with a unique composition. Accordingly, the electrodes 102 of the array 100 may extend through different carrier materials, and the conductive tip ends 104 may be placed throughout the different layers. Thus, in some embodiments, each electrode 102 is individually configured based on the corresponding layers of the carrier medium 112.

Electrode 102 characteristics may also be based on the intended function of the electrode 102. In further examples, because electrode surface area is inversely proportional to interface impedance, in some embodiments, a width 116 of an electrode 102 is selected based on the amount of stimulation to be delivered, the sensitivity of the target structure 110 to stimulation, and/or the sensitivity of the electrode 102 to the electrical behavior of the target structure 110. In another embodiment, the profile of an electrode is adapted to penetrate the carrier medium 112 such that a sharper electrode 102 profile is associated with a more resilient carrier medium 112 while a more rounded profile is associated with a more fragile carrier medium 112. In further embodiments, the electrode 102 characteristics are selected based on the above considerations, other relevant considerations, and/or combinations thereof. In this way, the present disclosure provides an array 100 of individually configurable electrodes 102, each adapted to the respective electrode environment and function.

Figure 1C:
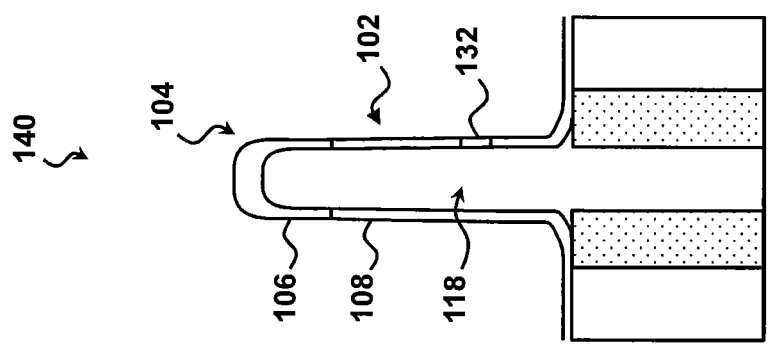
Figure 1B:
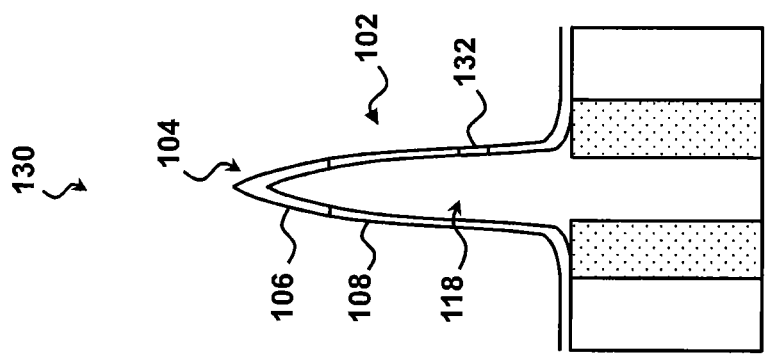

Electrode 102 configurations are disclosed in further detail with reference to FIGS. 1B, 1C, and 1D. As each electrode 102 of an array may be individually configured, a particular array may include electrodes 102 corresponding to one, several, or all of the profiles of FIGS. 1B, 1C, and 1D. FIG. 1B is a cross-sectional view of a multi-electrode array (MEA) 130 according to various aspects of the present disclosure. The multi-electrode array 130 includes one or more needle-type electrodes 102. A needle-type electrode 102 has an elongate body that tapers to a point at the tip end 104. The narrow tip end 104 allows the electrode 102 to easily penetrate a carrier medium 112 and provides a narrowly focused conductive tip for fine measurements and targeted stimulation. In that regard, the needle-type electrode 102 may include a conductive interface layer 106, a jacket layer 108, and an electrode core 118 substantially similar to those of FIG. 1A. In some embodiments, the electrode 102 includes secondary conductive areas 132 that are physically separated from the tip end 104 and the conductive interface layer 106. These provide additional stimulation and measurement sites. These secondary conductive areas 132 may be regularly or irregularly shaped and may take the form of cavities in the jacket layer 108 that expose the electrode core 118. The cavities may be filled with a conductive material electrically coupled to the electrode core 118 or the cavities may be left as open pores.

FIG. 1C is a cross-sectional view of a multi-electrode array (MEA) 140 according to various aspects of the present disclosure. The multi-electrode array 140 includes one or more pillar-type electrodes 102. A pillar-type electrode 102 has an elongate body with a blunt tip end 104. The blunt tip end 104 reduces the tendency of the electrode 102 to over penetrate a carrier medium 112 and provides a large contact area, thus reducing both resistance and charge density at the tip end 104. This type of profile may be well-suited to sensitive measurements and large stimulation voltages. In that regard, the pillar-type electrode 102 may include a conductive interface layer 106, a jacket layer 108, and an electrode core 118 substantially similar to those of FIG. 1A. In some embodiments, the electrode 102 includes secondary conductive areas 132 that are physically separated from the tip end 104 and the conductive interface layer 106. These provide additional stimulation and measurement sites. These secondary conductive areas 132 may be regularly or irregularly shaped and may take the form of cavities in the jacket layer 108 that expose the electrode core 118. The cavities may be filled with a conductive material electrically coupled to the electrode core 118 or the cavities may be left as open pores.

FIG. 1D is a cross-sectional view of a multi-electrode array (MEA) 150 according to various aspects of the present disclosure. The multi-electrode array 150 includes one or more dual-conical-type electrodes 102. A dual-conical electrode 102 has an elongate body with a tip end 104 comprising a roughly frustoconical region 152 and a roughly conical region 154 aligned in opposite orientations. The dual-conical tip end 104 penetrates a carrier medium 112 and allows the medium 112 to re-expand behind the frustoconical region 152 to retain the tip end 104 in place. This retention force makes the dual-conical electrode 102 suitable for use as a securing mechanism, anchoring the array 150 to the medium 112. Accordingly, in some embodiments, the multi-electrode array 150 includes dual-conical electrodes 102 at anchor locations such as around the periphery of the array 150. The dual-conical electrode 102 may include a conductive interface layer 106, a jacket layer 108, and an electrode core 118 substantially similar to those of FIG. 1A. In some embodiments, the electrode 102 includes secondary conductive areas 132 that are physically separated from the tip end 104 and the conductive interface layer 106. These provide additional stimulation and measurement sites. These secondary conductive areas 132 may be regularly or irregularly shaped and may take the form of cavities in the jacket layer 108 that expose the electrode core 118. The cavities may be filled with a conductive material electrically coupled to the electrode core 118 or the cavities may be left as open pores.

Figure 2:
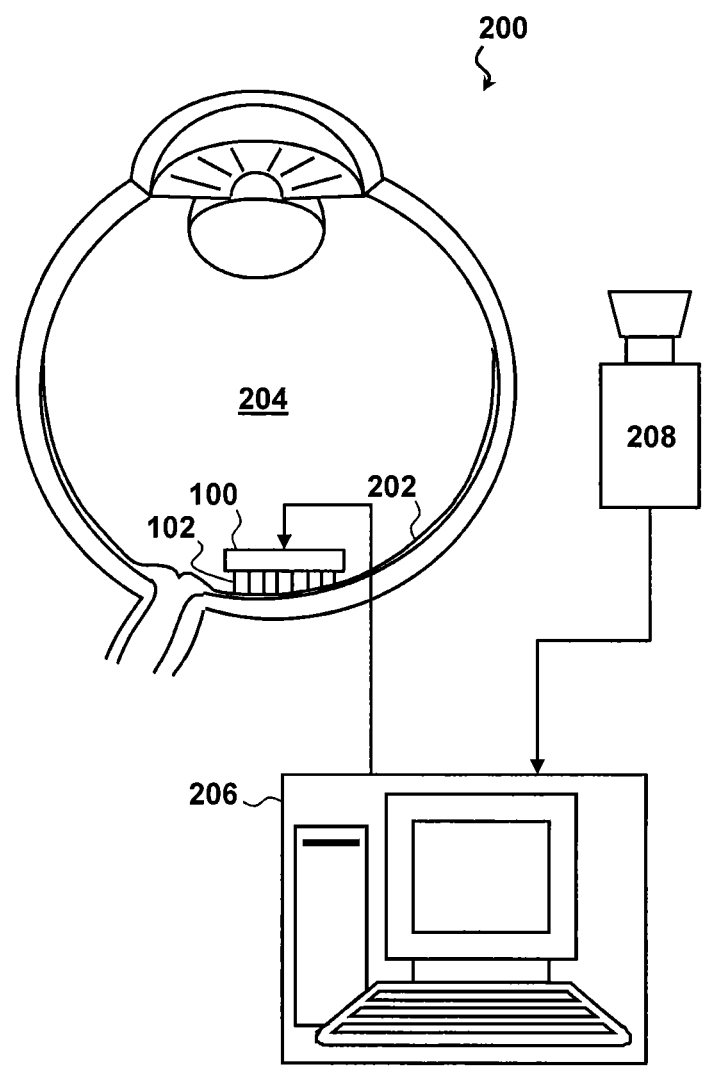
FIG. 2 is a diagrammatic illustration of a treatment for visual deficits according to various aspects of the present disclosure.

FIG. 2 is a diagrammatic illustration of a treatment 200 for visual deficits according to various aspects of the present disclosure. FIG. 2 has been simplified for the sake of clarity to better illustrate the inventive concepts of the present disclosure. Some visual impairments, such as macular degeneration and retinitis pigmentosa, render the retina unable to respond to light while leaving the neural pathways of the retina, optic nerve, and other visual processing structures intact. Macular degeneration and retinitis pigmentosa are typically progressive, beginning with a gradual reduction in vision but cumulating in profound vision loss. The effects are often irreversible, with time making the deficit more severe. In some embodiments of a treatment 200 for such impairments, a multi-electrode array 100 is utilized to electrically stimulate areas of the retina in order to provide the brain with visual information. In one such embodiment, electrodes 102 of the multi-electrode array 100 conduct the stimulation around or through the degenerated regions of the retina 202.

The retina 202 of an eye 204 is first analyzed to determine regions of the retina 202 to stimulate. Once the regions are identified, the electrodes 102 of a multi-electrode array 100 are configured to deliver electrical stimulation to the target regions. The target regions may be located at varying depths and varying spacing within the retina 202, and aspects of each electrode 102 may be individually tailored. This may include specifying electrode height, width, shape, spacing, the amount of the electrode tip covered by a conductive interface layer 106, and/or other electrode characteristics in order to bring the conductive portion of the electrode 102 into contact with a particular target region. Accordingly, the multi-electrode array 100 may be custom tailored to the patient's retina 202.

Once the configured array 100 is assembled, the array 100 is surgically implanted in contact with the retina 202. An integrated circuit device 206, which may take the form of an ASIC, FPGA, DSP, microcontroller, CPU, system on a chip (SOC), and/or other suitable computing device, sends electrical signals to the retina 202 using the array 100. The electrical signals stimulate the target structures retina 202 in order to simulate normal vision. In an exemplary embodiment, the integrated circuit device 206 receives images from an optical sensor 208, such as a charge-coupled device (CCD) array. The received images are translated into a sequence of electrical impulses that are administered to the retina 202 via the array 100. These impulses stimulate the retina 202 and create visual information similar to natural vision. In this way, the treatment 200 allows the patient to "see" a representation of the image captured by the optical sensor 208, thereby restoring a semblance of vision in an otherwise blind patient. It is understood of course that the exemplary treatment 200 is merely one possible use for the multi-electrode array 100, and that other uses such as deep brain stimulation, myoelectric control, and neuromuscular electrical stimulation are contemplated and provided for.

Figure 3A:
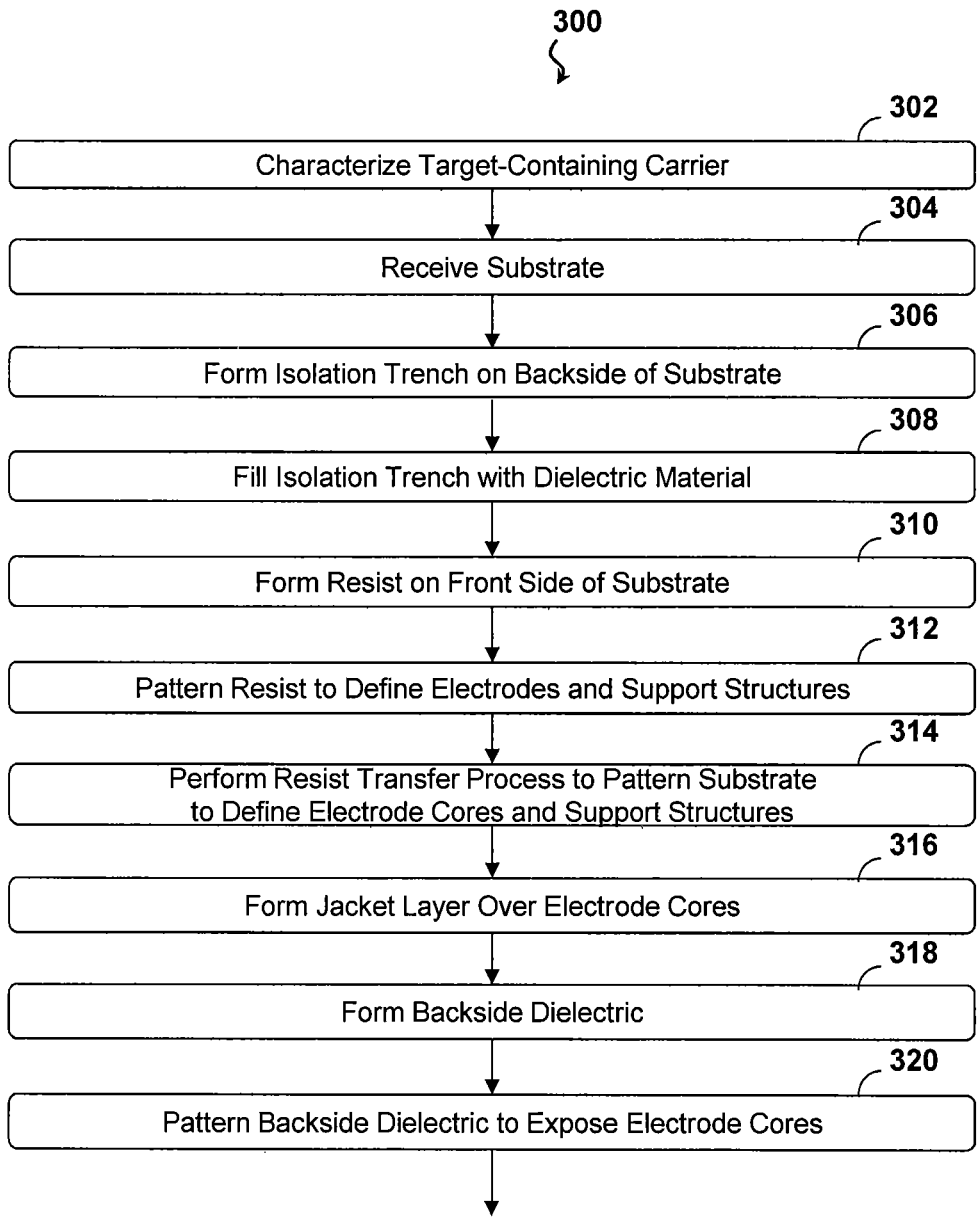
FIGS. 3A and 3B are flow diagrams of a method for forming a multi-electrode array according to various aspects of the present disclosure.
Figure 3B:
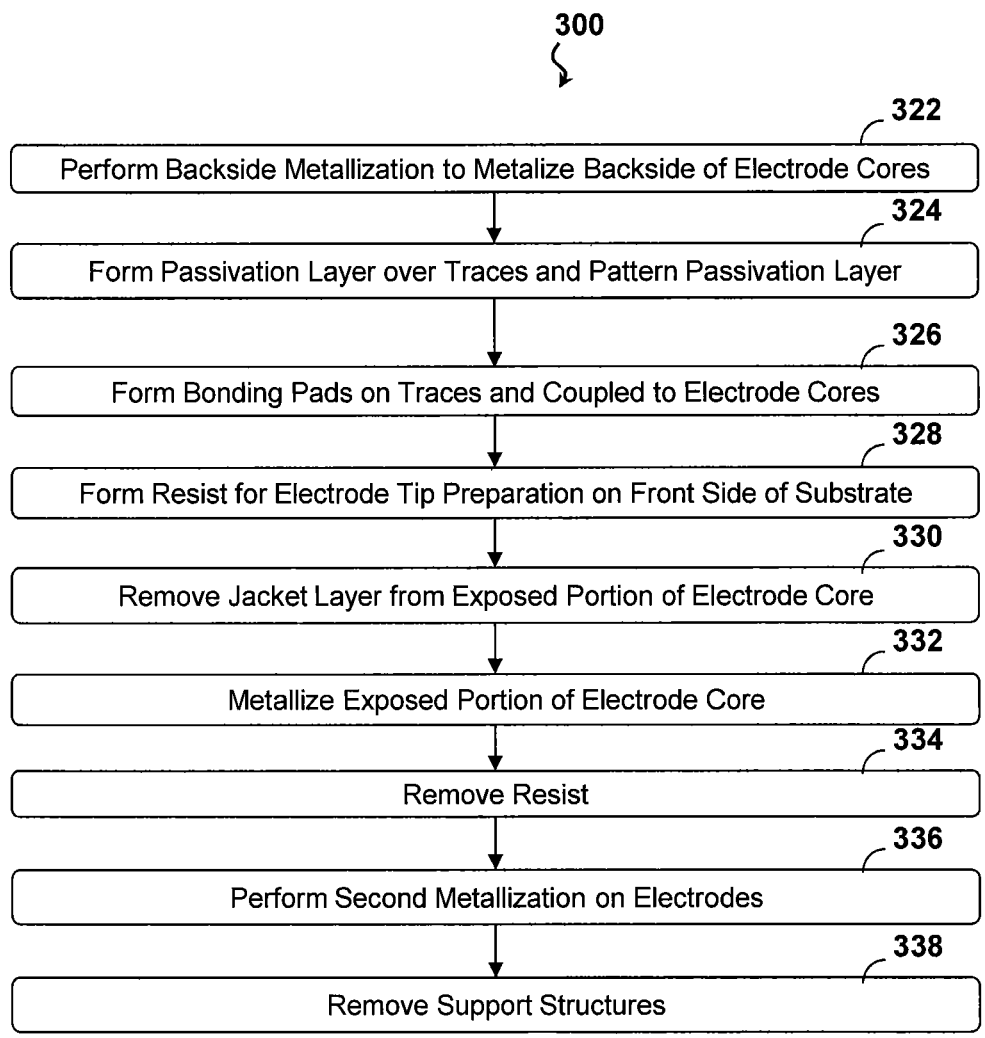
Figure 4:
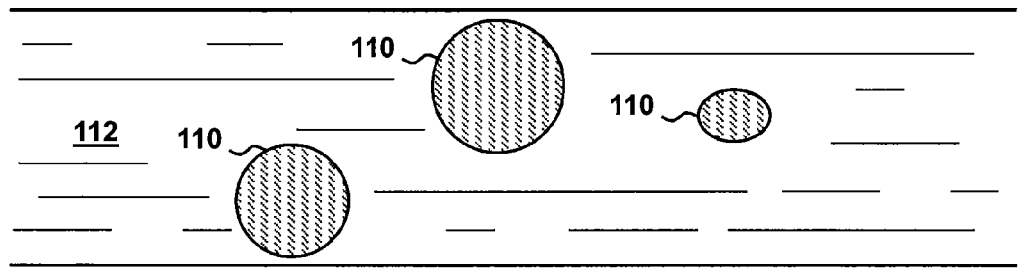
FIG. 4 is a diagrammatic cross-sectional view of a target-containing carrier according to various aspects of the present disclosure.

A method 300 of forming a multi-electrode array 100 adapted for a particular carrier 112 is disclosed with reference to FIGS. 3A and 3B and FIGS. 4-19. FIGS. 3A and 3B are flow diagrams of the method 300 for forming the multi-electrode array 100 according to various aspects of the present disclosure. It is understood that additional steps can be provided before, during, and after the method 300, and some of the steps described can be replaced or eliminated for other embodiments of the method 300. FIG. 4 is a diagrammatic cross-sectional view of a target-containing carrier 112 according to various aspects of the present disclosure. FIGS. 5-19 are diagrammatic cross-sectional views of the multi-electrode array 100 according to various aspects of the present disclosure. FIGS. 4-19 have been simplified for the sake of clarity to better illustrate the inventive concepts of the present disclosure.

Referring to FIG. 4 and block 302 of FIG. 3A, a target-containing carrier 112 is characterized. In some embodiments, the target-containing carrier 112 is a biological tissue such as retinal tissue, nervous tissue, cerebral tissue, muscle tissue, epithelial tissue, and/or other types of biological tissue known to one of ordinary skill in the art. In some embodiments, the carrier 112 includes multiple layers of varying composition such as epithelial tissue layers overlying muscle tissue layers. In further embodiments, the carrier 112 includes inorganic materials.

Dispersed throughout the carrier 112 are one or more target structures 110. Target structures 110 identify regions where an electrode tip is to be placed. In various embodiments, target structures 110 correspond to regions where measurements are to be taken and/or stimulation is to be provided. Characterizing the carrier 112 may include determining spatial orientations of individual target structures 110 within the carrier 112. In some embodiments, target size, target spacing, target depth within the carrier 112, and/or other spatial measurements are taken for each target structure 110. Characterizing the carrier 112 may also include determining the resilience of the carrier 112 and/or a target structure 110 to a sharp electrode. For example, resilient carriers 112 may suggest the use of sharper electrodes, whereas more fragile carriers 112 or target structures 110 may suggest the use of an electrode with a blunt profile. In some embodiments, characterizing the carrier 112 includes determining regions of the carrier 112 proximal to the target structures 110 where the electrodes are not to contact. In various further embodiments, characterizing the carrier 112 includes determining other suitable and relevant characteristics of the carrier 112 and/or the target structure 110.

Figure 5:
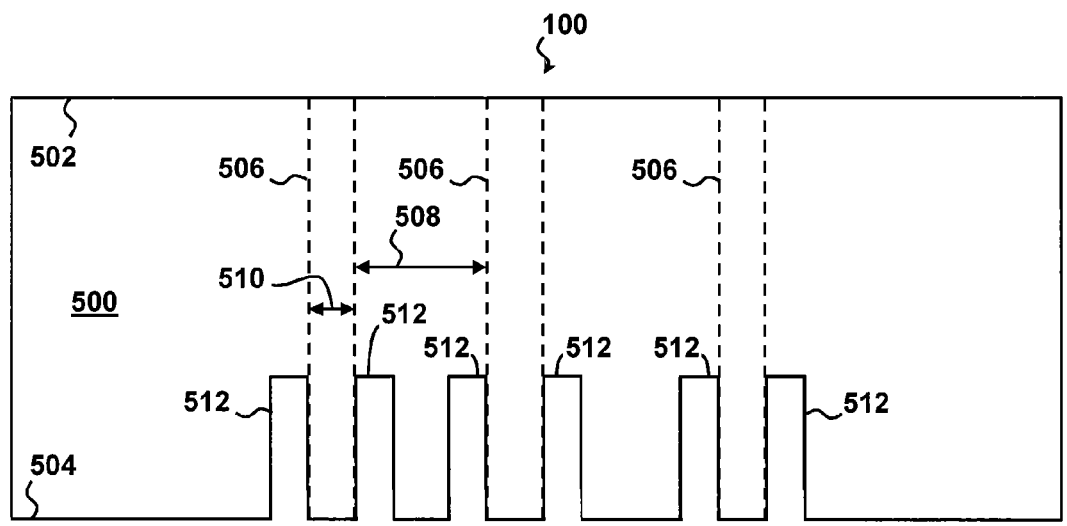
FIGS. 5-19 are diagrammatic cross-sectional views of a multi-electrode array undergoing the method for forming the array according to various aspects of the present disclosure.

Referring to FIG. 5 and block 304 of FIG. 3A, a substrate 500 for use in forming the multi-electrode array 100 is received. In various embodiments, the substrate 500 includes an elementary semiconductor such as silicon or germanium and/or a compound semiconductor, such as silicon germanium, silicon carbide, gallium arsenide, indium arsenide, gallium nitride, and indium phosphide. In some embodiments, the substrate 500 includes an alloy semiconductor, such as silicon germanium carbide, gallium arsenic phosphide, and gallium indium phosphide. The substrate 500 may also comprise non-semiconductor materials including soda-lime glass, fused silica, fused quartz, calcium fluoride ($CaF_2$), and/or other suitable materials. In various embodiments, the substrate 500 may take the form of a planar substrate, a fin, a nanowire, and/or other forms known to one of ordinary skill in the art. For clarity of disclosure, the substrate 500 includes a surface designated as a front side 502 and surface designated as a backside 504.

The substrate 500 includes regions 506 corresponding to the electrodes to be formed from the substrate 500. Accordingly, aspects of the regions 506 including size, shape, spacing, and/or other suitable aspects may depend on characteristics of the carrier 112 determined in block 302 of FIG. 3A. In an exemplary embodiment, the spacing 508 between two regions 506 corresponds to a spacing between two target structures 110 disposed within the carrier 112. In an exemplary embodiment, the width 510 of a region 506 corresponds to the width of a target structure 110 of the carrier 112. In further embodiments, other characteristics of the regions 506 correspond to other aspects of the carrier 112. The regions 506 each contain a conductive material, and in some embodiments, the conductive material extends from the front side 502 of the substrate 500 to the backside 504. In some embodiments, the bulk of the substrate 500 is non-conductive while the regions 506 are conductive. In further embodiments, the substrate 500 is conductive throughout. Because a conductive substrate 500 may cause electrical shorts between electrodes, isolation structures may be formed in the substrate 500 to insulate the conductive regions 506 from the bulk of the substrate 500 and from each other.

Referring to block 306 of FIG. 3A, an isolation trench 512 is formed on the backside 504 of the substrate 500. The isolation trench 512 is configured such that when an electrode 102 is eventually formed in a region 506, the electrode 102 is electrically isolated from the bulk of the substrate and from other electrodes in other regions 506. In some embodiments, the isolation trench may leave one or more sets of regions 506 electrically coupled while electrically isolating the sets from one another other. In other words, electrodes 102 may be grouped by electrically shorting the electrodes 102 of the group while isolating the electrodes from those of other groups.

Forming the isolation trench 512 may include forming and developing a photoresist coating. For example, in an embodiment, photoresist coating is applied using a spin-on technique. The photoresist coating is then exposed and developed in a process that may include soft baking, mask aligning, exposure, post-exposure baking, developing the photoresist, rinsing, drying (e.g., hard baking), and/or other suitable photolithographic steps. Alternatively, the photolithographic process may be implemented, supplemented, or replaced by other methods such as maskless photolithography, electron-beam writing, and ion-beam writing. In the exemplary embodiment, the development of the photoresist coating exposes areas of the substrate 500 to be etched to form the isolation trenches 512. The substrate 500 is then etched using any suitable removal processes including dry etching, wet etching, and/or other etching methods (e.g., ashing, reactive ion etching, etc.). In an exemplary etching process, an anisotropic etching is performed using potassium hydroxide (KOH). In a further exemplary etching process, an anisotropic deep reactive ion etching (DRIB) is performed. The etching may be performed to any suitable depth, and in the illustrated embodiment, the isolation trenches 512 extend a partial thickness of the substrate 500. For example, in an embodiment utilizing a substrate 500 having a thickness of approximately 400 μm, an isolation trench 512 is etched to a depth of approximately 250 μm.

Figure 6:
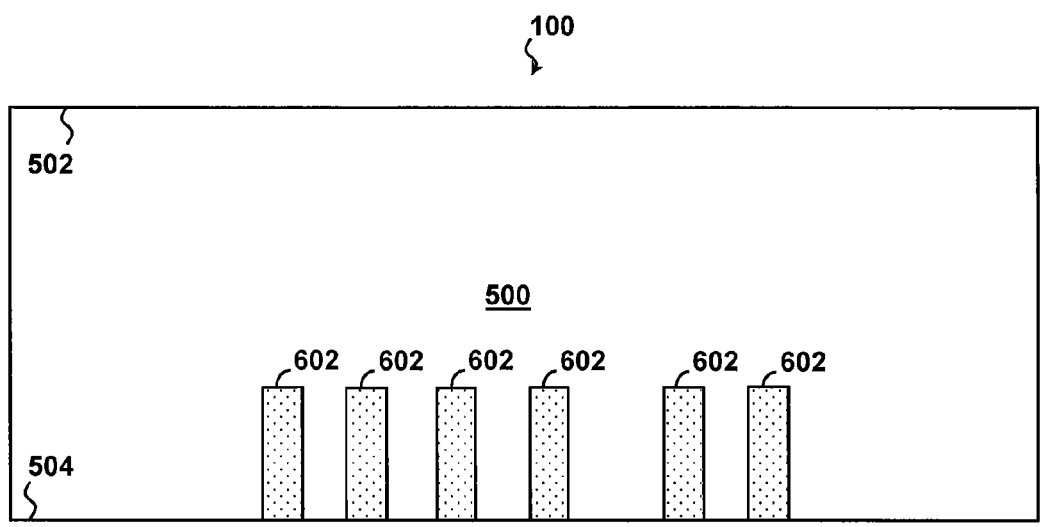

Referring to FIG. 6 and block 308 of FIG. 3A, the isolation trench 512 is filled with a dielectric material 602 to form an isolation feature. The isolation features electrically isolates the electrodes 108 of the finished array 102 from each other. The dielectric material 602 may include a semiconductor oxide, a semiconductor oxynitride, a semiconductor nitride, other suitable dielectric fill materials, non-dielectric fill materials, and/or combinations thereof. The dielectric material 602 may be formed using high-density plasma chemical vapor deposition (HDP), a high-aspect ratio process (HARP), another suitable process, and/or a combination thereof. In some embodiments, the dielectric material 602 has a multilayer structure, such as a liner and a fill material formed on the liner. Exemplary liners include semiconductor oxides and may be formed by thermal oxidation, chemical vapor deposition (CVD), physical vapor deposition (PVD), atomic layer deposition (ALD), other suitable processes, and/or combinations thereof.

Figure 7:
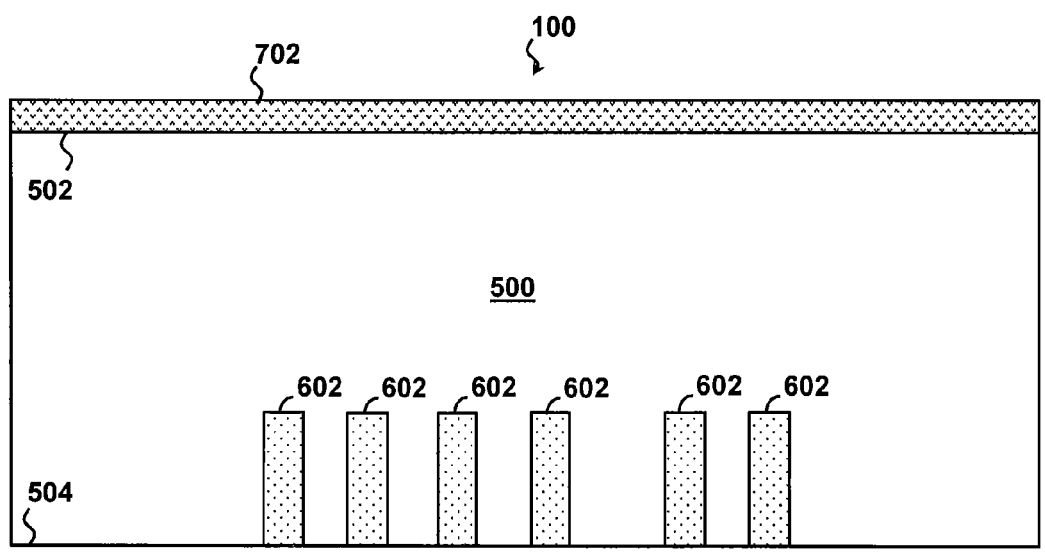

Referring to FIG. 7 and block 310 of FIG. 3A, a resist 702 is formed on the front side 502 of the substrate 500. The resist 702 may be formed by any suitable process to any suitable thickness. In an exemplary embodiment, the resist 702 is a photoresist and is formed using a spin-on process. The resist 702 is used to define electrode cores 118, which may be performed in a single pass etching process such as the process disclosed with reference to FIGS. 8A and 8B or in an iterative etching process such as the process disclosed with reference to FIGS. 9A, 9B, 9C, and 9D. For conciseness, the process of FIGS. 9A, 9B, 9C, and 9D disclose two iterations of etching although the principles of the present disclosure apply equally to embodiments with any number of iterations.

Figure 8A:
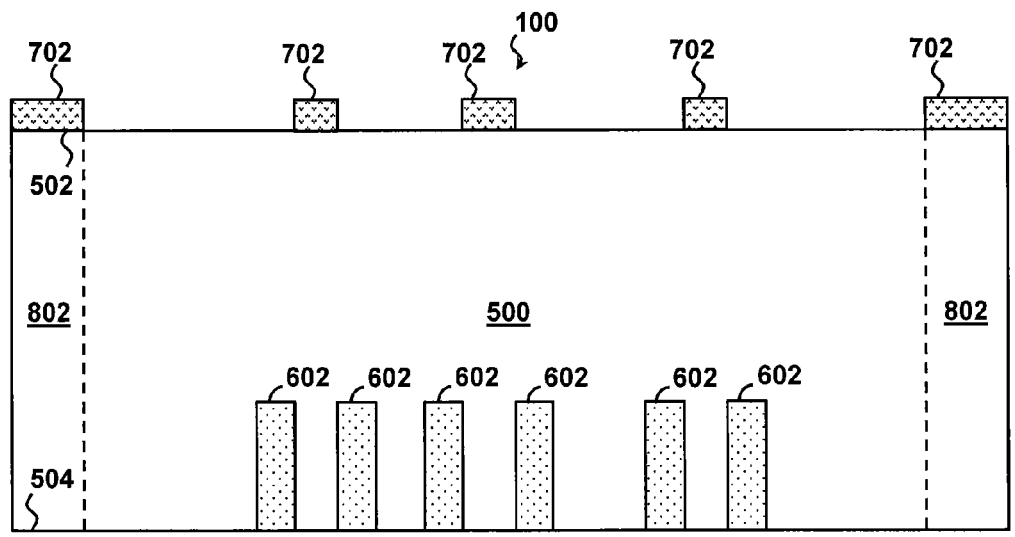

Referring first to FIG. 8A and block 312 of FIG. 3A, the resist 702 is patterned. Because structures formed by the patterned resist 702 interface with structures formed on the backside 504 of the substrate 500, patterning may include a front-to-back alignment to ensure that the structures formed on the front side 502 of the substrate are properly positioned. This may be performed using any suitable alignment technique to any suitable tolerance.

In some embodiments, patterning of the resist 702 includes soft baking, mask aligning, exposure, post-exposure baking, developing the photoresist, rinsing, drying (e.g., hard baking), and/or other suitable photolithographic steps. Alternatively, the photolithographic process may be implemented, supplemented, or replaced by other methods such as maskless photolithography, electron-beam writing, and ion-beam writing. In the exemplary embodiment, the development of the photoresist coating 702 exposes areas of the substrate 500 to be etched. The patterns of the remaining resist 702 regions determine characteristics of the electrodes 102 to be formed. Accordingly, the physical characteristics of the remaining resist 702 regions may be configured to control electrode width, height, shape, and/or other electrode characteristics as determined by the target structures 110 and the carrier 112. The characteristics of the remaining resist 702 (in conjunction with the backside isolation features) may also be configured to control electrode spacing or pitch. The lithographic electrode 102 formation of the method 300 allows much tighter electrode 102 spacing than, for example, sawing or dicing processes. In an exemplary embodiment, the electrodes 102 are formed to a pitch of less than or equal to about 100 µm between adjacent electrodes 102, and submicron electrode 102 pitches are achievable.

In some embodiments, the patterning of the resist 702 also defines one or more support structures 802. Support structures 802 provide physical protection for the electrodes 102 during fabrication and transportation and may be used as a mount point for a handle wafer during backside processing.

Figure 8B:
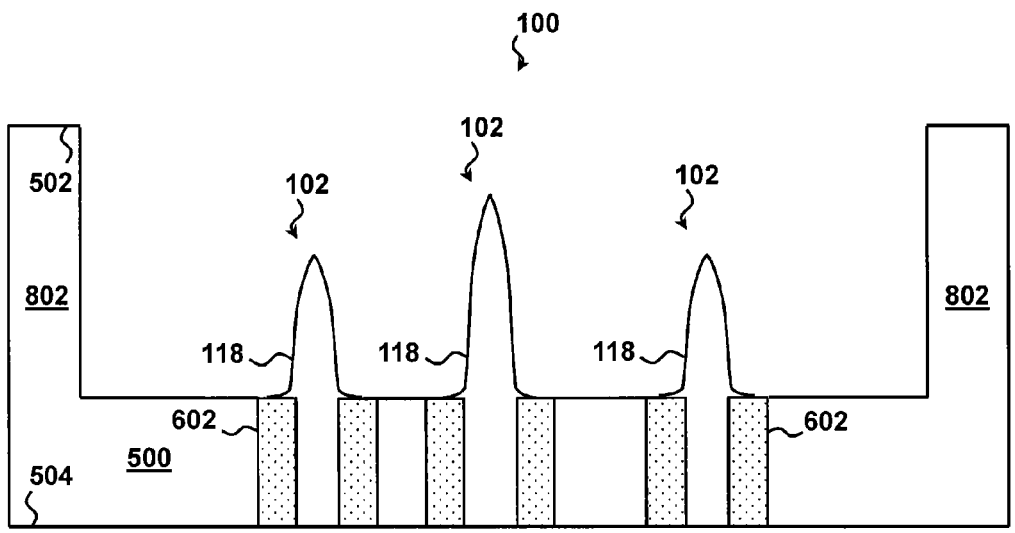

Referring to FIG. 8B and block 314 of FIG. 3A, the substrate 500 is patterned to form electrode cores 118 of the array 100, and, in some embodiments, support structures 802. The process may be referred to as a resist transfer process. Patterning of the substrate 500 may include etching the substrate 500 using any suitable processes including dry etching, wet etching, and/or other etching methods (e.g., ashing, reactive ion etching, etc.). In an exemplary etching process, an anisotropic etching is performed using potassium hydroxide (KOH). In a further exemplary etching process, an anisotropic deep reactive ion etching (DRIE) is performed. The etching may be performed to any suitable depth. For example, in an embodiment utilizing a substrate 500 having a thickness of approximately 400 µm, the substrate 500 is etched to a depth of 150 µm. Remaining resist 702 may be removed following the patterning of the substrate 500.

It is not necessary to form the electrode cores 118 concurrently. In many embodiments, the patterning of blocks 310-314 of FIG. 3A is repeated, and each iteration of the patterning forms a subset of the electrode cores 118. Process variables may be modified between iterations in order to produce greater diversity of electrode core 118 attributes. For example, etching parameters used in block 314 of FIG. 3A including time, temperature, etchant concentration, plasma field strength, and other process variables may differ between iterations. In a further example, the etching techniques of block 314 of FIG. 3A differ between iterations, such as a wet etching process used in a first iteration and a DRIE process used in a subsequent iteration. Thus, the patterning of blocks 310-314 of FIG. 3A may be repeated as needed to form the electrode cores 118.

Figure 9A:
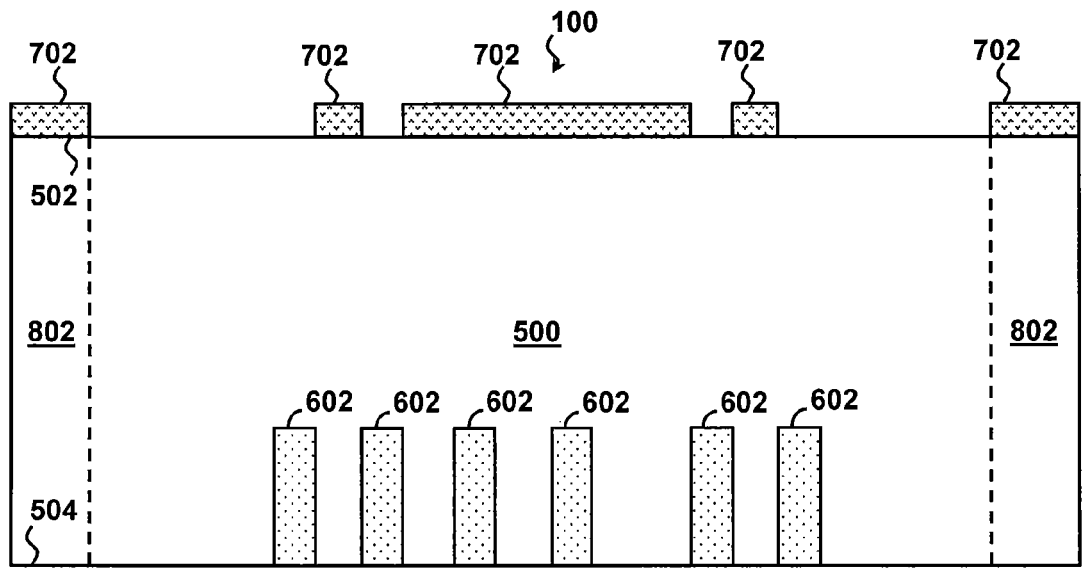
Figure 9B:
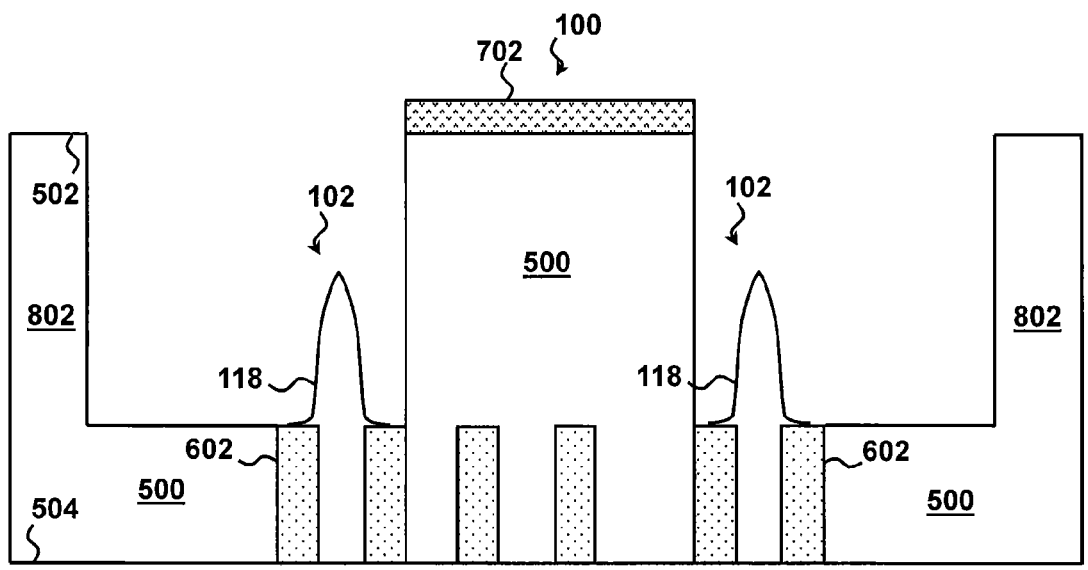

Referring to FIG. 9A and block 312 of FIG. 3A, the resist 702 is patterned to define a subset of the electrode cores 118 and to protect a region of the substrate corresponding to the remaining electrode cores 118. The patterning may proceed substantially similar to the process disclosed with reference to FIG. 8A and block 312 of FIG. 3A. Referring to FIG. 9B and block 314 of FIG. 3A, the substrate 500 is patterned to form the subset of electrode cores 118 defined by the resist 702. The patterning may proceed substantially similar to the process disclosed with reference to FIG. 8B and block 314 of FIG. 3A, and may include etching the substrate 500 using any suitable processes including dry etching, wet etching, and/or other etching methods (e.g., ashing, reactive ion etching, etc.). Remaining resist 702 may be removed following the patterning of the substrate 500.

Figure 9C:
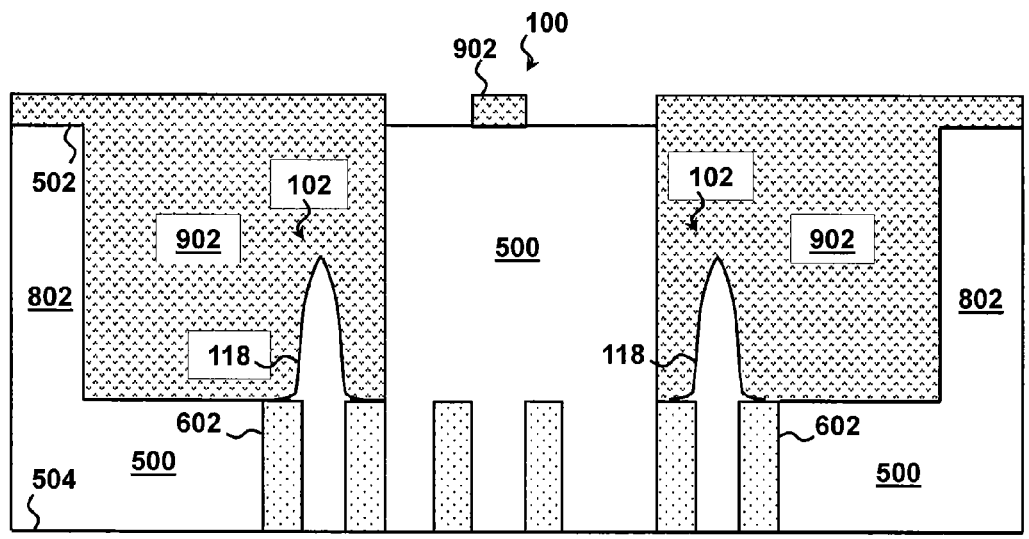
Figure 9D:
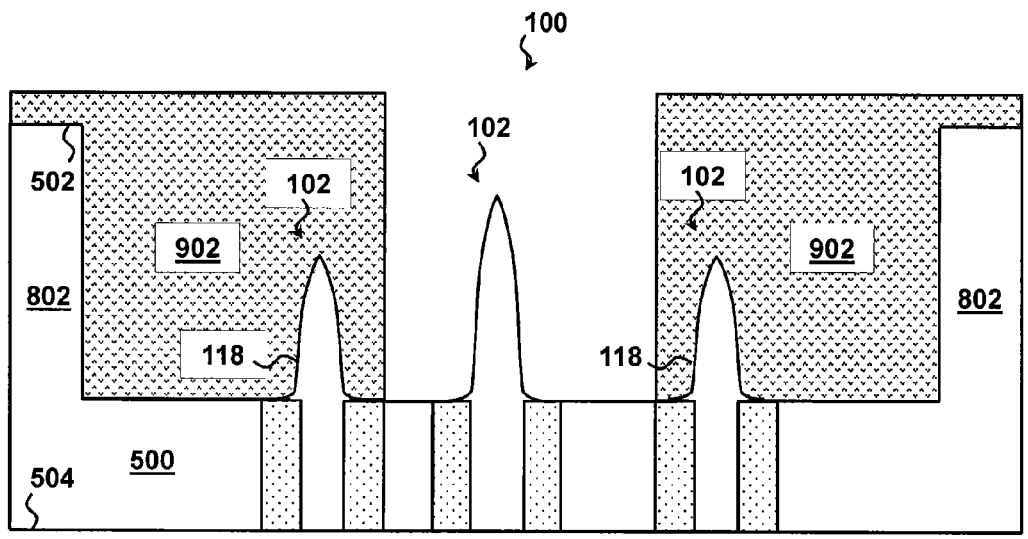

Referring to FIG. 9C and to block 310 of FIG. 3A, the subsequent iteration includes applying another resist 902. The resist 902 may be selected to have good gap filling properties in order to fill the space between the formed electrode cores 118 and the unpatterned portion of the substrate 500. Referring still to FIG. 9C and now to block 312 of FIG. 3A, the resist 902 is patterned to define a second subset of the electrode cores 118. The patterning may proceed substantially similar to the process disclosed with reference to FIG. 8A and block 312 of FIG. 3A. Finally, referring to FIG. 9D and to block 314 of FIG. 3A, the substrate 500 is again patterned to form the second subset of electrode cores 118 of the array 100. Remaining resist 902 may be removed following the patterning of the substrate 500.

Figure 10:
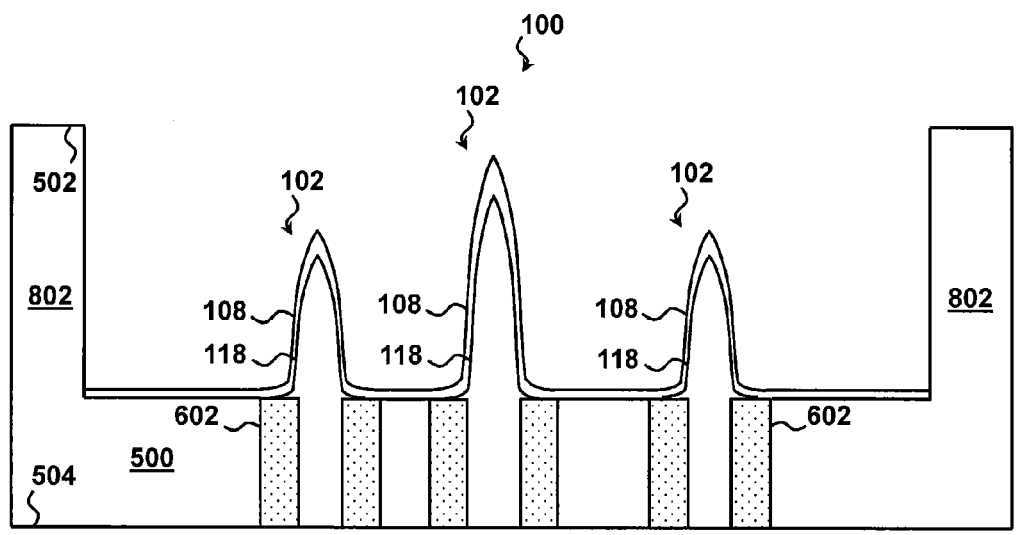

After forming the cores 118, referring to FIG. 10 and block 316 of FIG. 3A, a jacket layer 108 may be formed on at least a portion of the front side 502 of the substrate 500. In addition to electrically insulating conductive portions of the substrate 500, the jacket layer 108 may act as a physical barrier between the substrate 500 and a biological or other environment. The jacket layer 108 may also be used to protect the front side 502 of the substrate 500 during backside 504 processing. Thus in many embodiments, the jacket layer 108 includes a material that is electrically resistive, durable, biocompatible, and chemically inert. Suitable materials for the jacket layer 108 include a semiconductor oxide, a semiconductor carbide, a poly-para-xylylene material, a diamond coating material, and/or other materials known to one of ordinary skill in the art. The jacket layer 108 may have a multi-layer composition, for example a silicon nitride inner layer with a silicon oxide outer layer. The inner layer or layers may provide support, reduce strain and/or have better gap fill properties than the outer layers. In an embodiment, an inner layer that is not technically biocompatible is covered by a biocompatible outer layer. The jacket layer (or layers) 108 may be formed to any suitable thickness and may be formed by any suitable process including thermal oxidation, chemical vapor deposition (CVD), physical vapor deposition (PVD), atomic layer deposition (ALD), other suitable processes, and/or combinations thereof. In various embodiments, the jacket layer 108 is formed to a thickness of between about 50 nm and about 5 µm.

In some embodiments, the jacket layer 108 completely covers the electrode cores 118. In such embodiments, the jacket layer 108 may be subsequently etched back as disclosed below.

Figure 11:
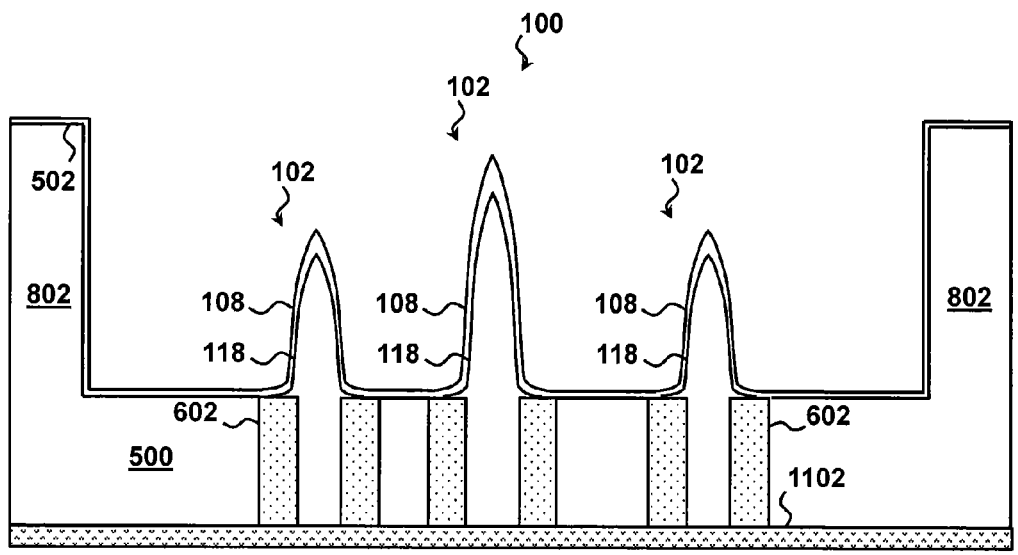

Referring to FIG. 11 and block 318 of FIG. 3A, a backside dielectric layer 1102 may be formed on the backside of the substrate 500. The backside dielectric layer 1102 may include a semiconductor oxide, a semiconductor oxynitride, a semiconductor nitride, polyimide, Parylene C, other suitable dielectric materials, and/or combinations thereof. In an embodiment, the backside dielectric layer 1102 includes a thermal oxide and is formed by oxidation at a temperature between approximately 1000° C. and approximately 1100° C.

In some embodiments, an intermediate dielectric layer (not shown) such as a native oxide and/or other protective dielectric is formed on the backside 504 of the substrate 500 and acts a temporary protective layer used during wafer handling and substrate processing. Native oxides occur naturally on some substrate 500 materials when exposed to air under ambient conditions, and thus the formation of the intermediate dielectric layer may be intentional or incidental. Because the intermediate dielectric material may impede the formation of a high-quality backside dielectric layer 1102, in some embodiments, the intermediate dielectric layer is removed via etching and the backside dielectric layer 1102 is deposited thereafter.

In block 320 of FIG. 3A, the backside dielectric layer 1102 is patterned to expose a portion of electrode cores 118. Patterning of the backside dielectric layer 1102 may include a photolithographic process (e.g., forming a photoresist coating, soft baking, mask aligning, exposure, post-exposure baking, developing the photoresist, rinsing, drying, and/or other suitable photolithographic steps) and may include a suitable etching process (e.g., dry etching, wet etching, ashing, and/or another etching method). The patterning allows electrical contact to be made to the electrode cores 118 via the backside 504 of the substrate 500.

Figure 12:
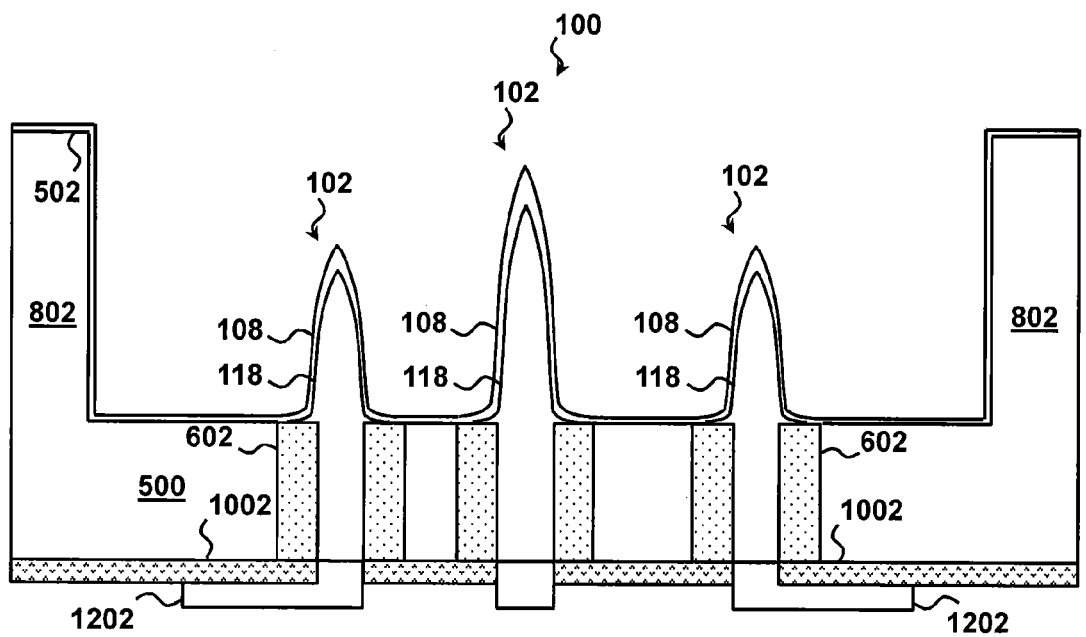

Referring to FIG. 12 and block 322 of FIG. 3B, a backside metallization is performed. The backside metallization forms conductive traces 1202 electrically coupled to the electrode cores 118. The conductive traces 1202 may include copper, aluminum, aluminum/silicon/copper alloy, titanium, titanium nitride, tungsten, nickel, polysilicon, metal silicide, other metallic and non-metallic conductive materials, and/or combinations thereof. The conductive traces 1202 may have a multilayer composition, and thus, in an exemplary embodiment, the conductive traces include a titanium layer formed to a thickness of at least approximately 90 nm and an aluminum layer formed to a thickness of approximately 1 µm. The conductive traces 1202 may be formed by one or more processes including sputtering, PVD, CVD, thermal annealing (commonly used to form metal silicides), photolithography, etching, and/or combinations thereof.

Figure 13:
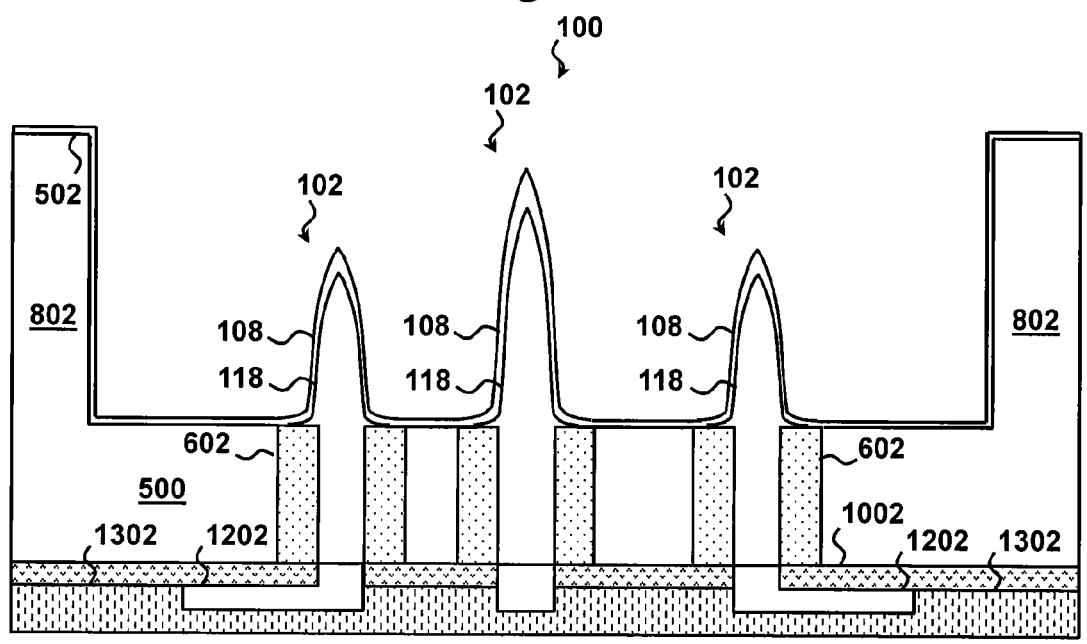

Referring to FIG. 13 and block 324 of FIG. 3B, a passivation layer 1302 may be formed on the conductive traces 1202. The passivation layer 1302 may include a dielectric such as a semiconductor oxide, a semiconductor oxynitride, a semiconductor nitride, or a combination thereof. In some embodiments, the passivation layer 1302 includes an insulator material such as a ceramic material, a polymer material, and/or a plastic material. The passivation layer 1302 may be formed by one or more processes including PVD, polarized electrochemical vapor deposition (PECVD), CVD, thermal annealing (commonly used to form metal silicides), photolithography, etching, and/or combinations thereof. In an exemplary embodiment, the passivation layer 1302 is a PECVD nitride and is formed to a thickness of approximately 1 µm. The passivation layer 1302 is patterned to expose portions of the conductive traces 1202, to allow the formation of bonding pads, and/or to contain molten solder during packaging.

Figure 14:
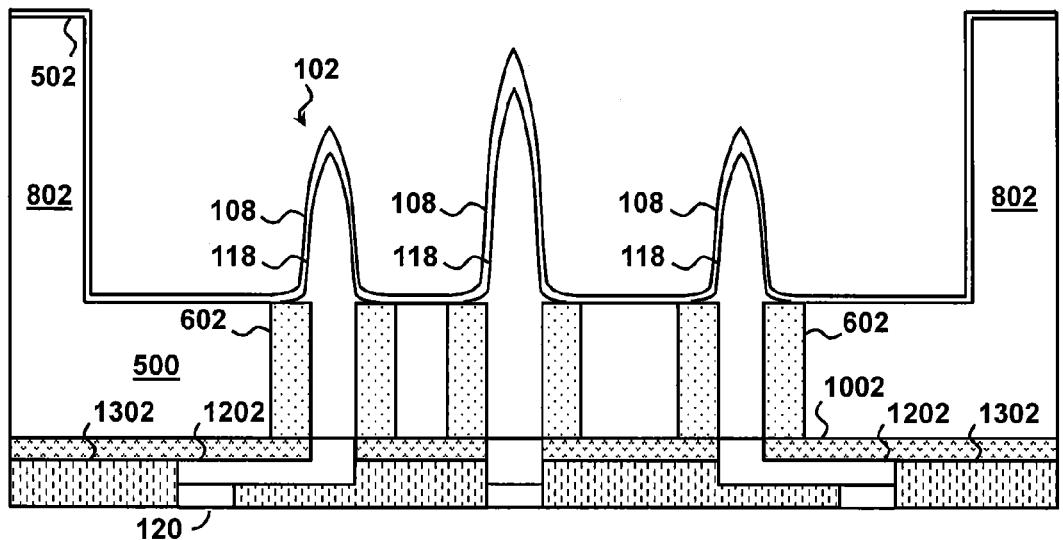

Referring to FIG. 14 and block 326 of FIG. 3B, bonding pads 120 are formed on the conductive traces 1202. The bonding pads are electrically coupled to the electrode cores 118 via the conductive traces 1202 and thereby provide a contact point for coupling the electrode cores 118 to other circuits (not shown). In the illustrated embodiments, the conductive traces 1202 couple the cores 118 to the bonding pads 120 and allow for configurations where the bonding pads 120 are directly aligned with the cores 118 as well as configurations where the bonding pads 120 and the conductive cores 118 are offset. In contrast, in an embodiment where the electrode cores 118 are aligned with the bonding pads 120, the pads 120 are formed directly on the cores 118 without an intervening conductive trace 1202.

In some embodiments, forming the bonding pads 120 includes patterning the passivation layer 1302 to expose portions of the conductive traces 1202 and/or electrode cores 118 to which the bonding pads 120 are to couple. The bonding pads 120 may include conductive materials, such as copper, aluminum, aluminum/silicon/copper alloy, titanium, titanium nitride, tungsten, nickel, polysilicon, metal silicide, other metallic and non-metallic conductive materials, and/or combinations thereof and may have a multilayer composition. In an exemplary embodiment, the bonding pads 120 include a nickel/aluminum alloy. The materials of the bonding pads 120 may be deposited by one or more processes including sputtering, PVD, CVD, thermal annealing (commonly used to form metal silicides), photolithography, etching, and/or combinations thereof.

Figure 15:
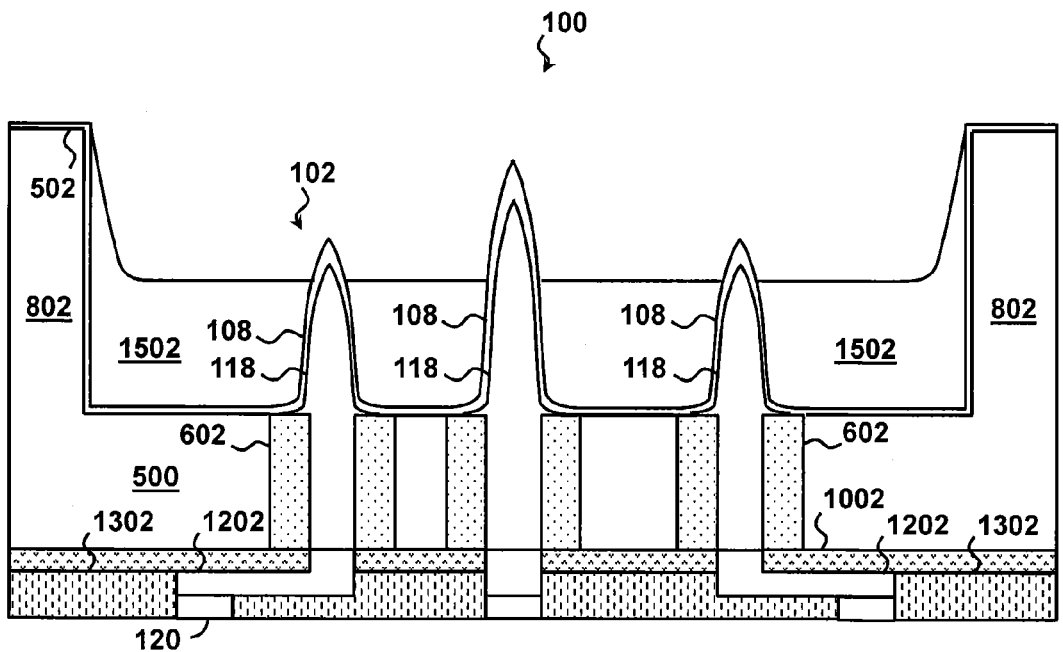

Referring to FIG. 15 and block 328 of FIG. 3B, a resist 1502 is formed on the front side 502 of the substrate 500 including between the electrodes 102. The resist 1502 is used to prepare the tip-ends of the electrodes 102, and thus the resist 1502 exposes the tip portion of an electrode core 118. In an embodiment, resist 1502 exposes approximately 30 µm at the tip-end of an electrode core 118. As the electrode cores 118 of the electrode array 100 may have different physical configurations, in some embodiments, the resist 1502 exposes different amounts of the various electrode cores 118. For example, the resist 1502 may expose approximately 30 µm of a first electrode core and 100 µm of a second electrode core. The resist 1502 may be formed using any suitable process including spin-on deposition, PVD, CVD, HDP-CVD, ALD, ink jet deposition, other suitable deposition processes, and/or combinations thereof.

Figure 16:
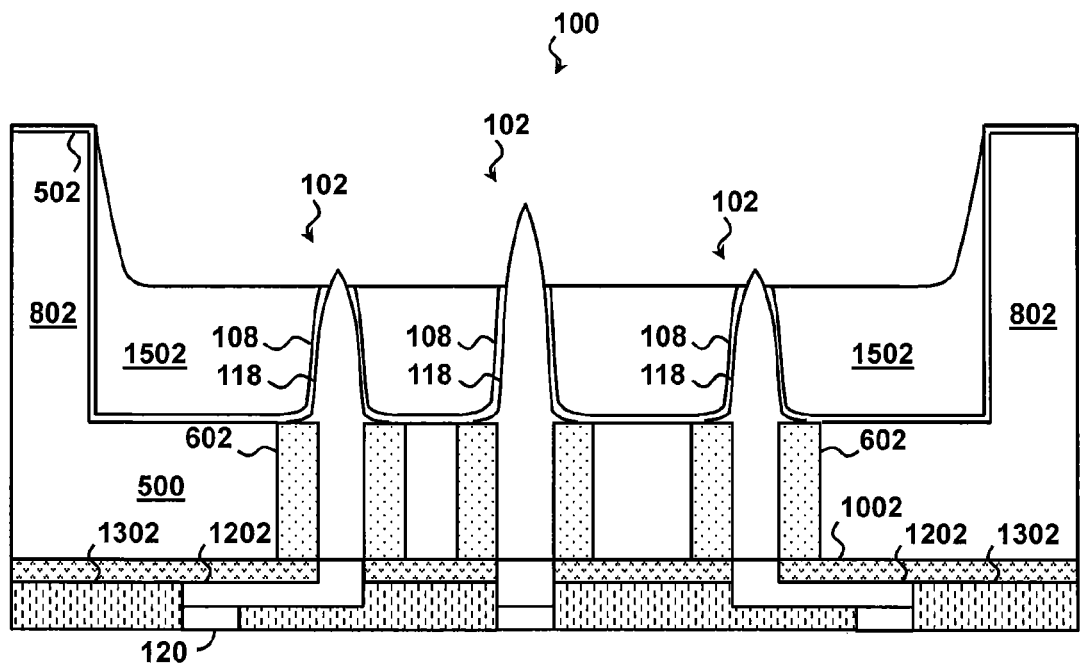

Referring to FIG. 16 and block 330 of FIG. 3B, the jacket layer 108 is removed from the exposed portion of the electrode cores 118. The jacket layer 108 may be removed via dry etching, wet etching, and/or other etching methods (e.g., ashing, reactive ion etching, etc.). In an exemplary etching process, the jacket layer 108 is removed using an ashing process. The removal of the jacket layer 108 exposes a portion of the conductive electrode core 118.

Figure 17:
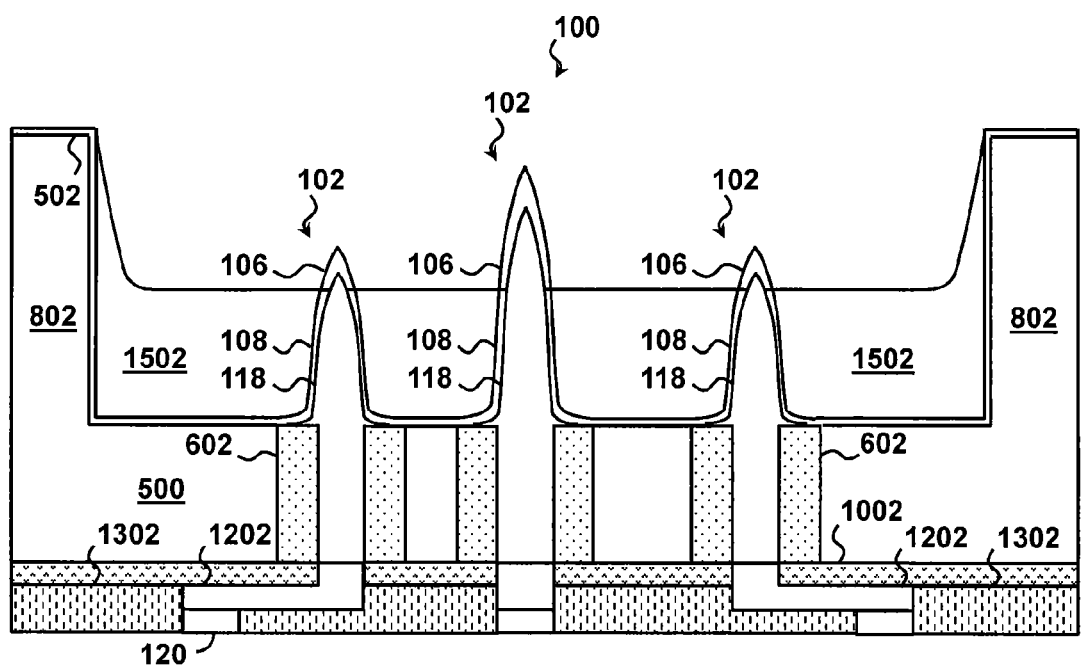

In some embodiments, the exposed portion of the electrode core 118 is left bare. In alternate embodiments, a conductive tip is formed over the exposed portion of the electrode core 118. Referring to FIG. 17 and block 332 of FIG. 3B, the exposed portion of the electrode core 118 is metallized. Metallization is not necessarily limited to the forming of purely metallic materials, and thus metallization may include forming a conductive interface layer 106 containing copper, aluminum, aluminum/silicon/copper alloy, titanium, titanium nitride, tungsten, nickel, polysilicon, metal silicide, other metallic and nonmetallic conductors such as PEDOT, and/or combinations thereof. The conductive interface layer 106 reduces electrical impedance at the interface between the electrode 102 and the target structure 110, and thus materials for the interface layer 106 may be selected to have a high ratio of electrochemically active surface area to geometric surface area. The materials for the interface layer 106 may also be selected for biocompatibility, resilience, durability, and other electrical and/or electrochemical factors. Accordingly, in an exemplary embodiment, the conductive tip includes one or more of titanium nitride (TiN), platinum, an iridium oxide, carbon structures including carbon graphene, carbon nanotubes, functionalized carbon nanotubes, and/or other suitable materials. The interface layer 106 may be formed via sputtering, PVD, CVD, thermal annealing (commonly used to form metal silicides), photolithography, etching, laser ablation, and/or combinations thereof.

In order to further reduce electrical impedance at the interface between the electrode 102 and the target structure 110, the interface layer 106 may be patterned or roughened to further increase the electrochemically active surface area. In an embodiment, laser ablation is used to pattern the surface of the interface layer 106. In a further embodiment, an etchant is used to create surface imperfections in the interface layer 106. Other suitable processes including chemical roughening, mechanical roughening, deposition, and/or electroplating may also be used to shape the surface of the interface layer 106.

Referring to block 334 of FIG. 3B, the resist 1502 is stripped. In some embodiments, the resist 1502 is stripped prior to the metallization of block 332 of FIG. 3B. In alternate embodiments, the resist 1502 is stripped subsequent to the metallization of block 332 of FIG. 3B.

Figure 18:
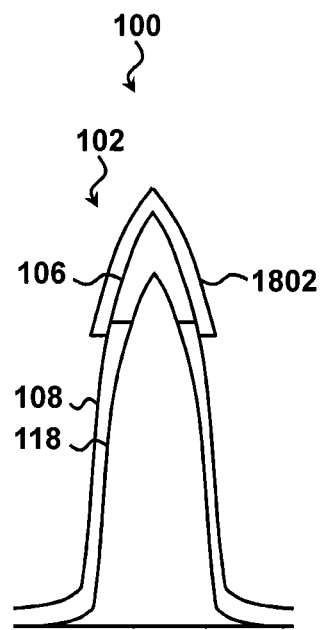

Referring to FIG. 18 and block 336 of FIG. 3B, a second metallization may be performed on the electrodes 102. The second metallization applies a second conductive layer 1802 over the interface layer 106. The second conductive layer 1802 physically reinforces the tip-end of the electrode 102 and may fill any gap that occurs at the interface between the interface layer 106 and the jacket layer 108. In that regard the second conductive layer 1802 may include copper, aluminum, aluminum/silicon/copper alloy, titanium, titanium nitride, tungsten, nickel, polysilicon, metal silicide, other metallic and nonmetallic conductors such as PEDOT, and/or a combination thereof, and the conductive material of the second conductive layer 1802 may be the same as or different from the material of the interface layer 106. In an exemplary embodiment, the second conductive layer 1802 includes one or more of titanium nitride (TiN), platinum, an iridium oxide, carbon structures including carbon graphene, carbon nanotubes, functionalized carbon nanotubes, and/or other suitable materials. The second conductive layer 1802 may be formed via sputtering, PVD, CVD, thermal annealing (commonly used to form metal silicides), photolithography, etching, laser ablation, chemical functionalization, and/or combinations thereof.

Figure 19:
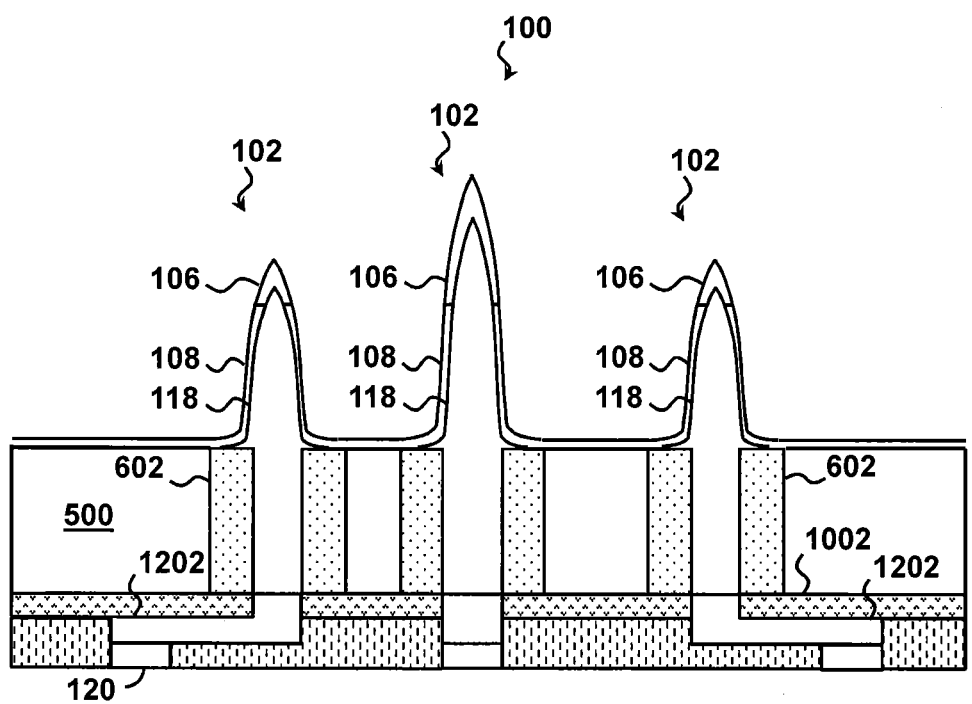

Referring to FIG. 19 and block 338 of FIG. 3B, the support structures 802 may be removed from the array 100. In some embodiments, the support structures 802 are removed during the dicing that separates the array 100 from the remainder of the substrate 500. In one such embodiment, a dicing tape is applied to the array 100 to retain and secure the array 100 during a mechanical sawing procedure. In other such embodiments, laser cutting and/or deep-reactive ion etching is used to remove the support structures 802. In further embodiments, removal of the support structures 802 includes other suitable dicing processes known to one of ordinary skill in the art.

Figure 20:
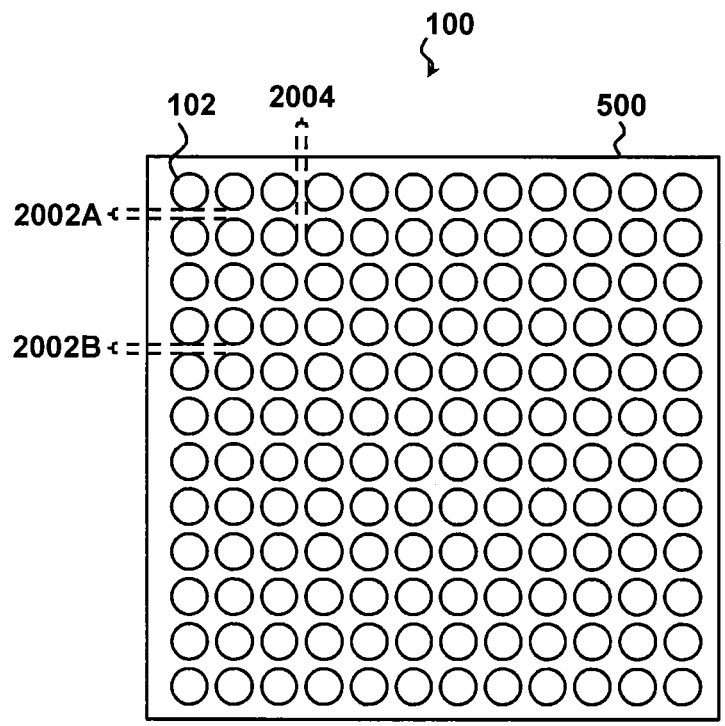
FIGS. 20-24 are top views of multi-electrode arrays according to various aspects of the present disclosure.

FIG. 20 is a top view of a multi-electrode array 100 according to various aspects of the present disclosure. The array 100 may be substantially similar to that disclosed with reference to FIGS. 1-19. In that regard, the array 100 includes a plurality of electrodes 102 arranged on a substrate 500. In the illustrated embodiment, the array 100 includes a 12×12 arrangement of electrodes 102. However, the array 100 may contain any suitable number of electrodes 102 in any suitable arrangement. For example, in a further embodiment, the array 100 includes a 128×128 arrangement of electrodes.

The electrodes 102 are sized and structured to contact target structures located in a carrier medium (e.g., the carrier medium 112 of FIGS. 1 and 4). Because the target structures may vary in size and shape and may be distributed throughout the carrier medium, aspects of the electrodes 102 including height, width, amount of the electrode covered by a conductive interface layer 106, electrode shape, spacing between electrodes, and/or other electrode characteristics may be configured to bring an electrode 102 in contact with a particular target structure. As merely one example, electrode spacing may vary throughout the array. That is, a first electrode spacing 2002A may be different from or substantially similar to a second electrode spacing 2002B based on considerations including characteristics of the carrier medium and/or the respective target structures. Likewise, an electrode spacing in a first direction (e.g., spacing 2002A) may be different from or substantially similar to an electrode spacing in a second direction (e.g., spacing 2004) based on similar considerations. In this way, the electrodes 102 can be adapted to a particular target-containing medium.

Figure 21:
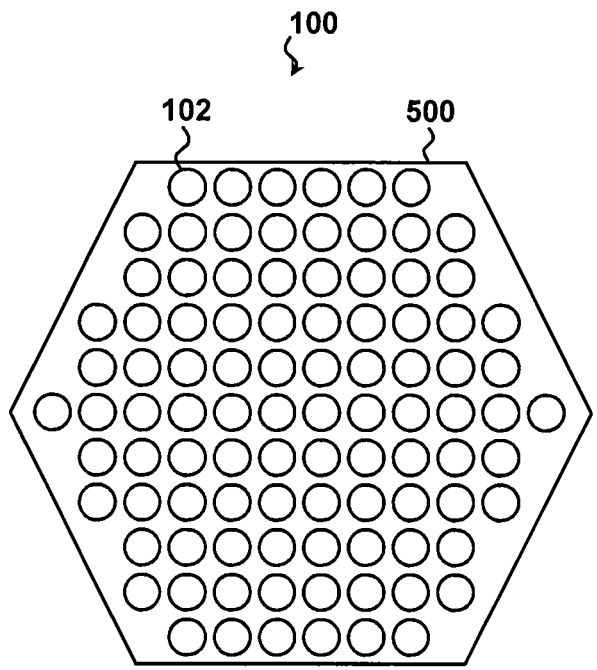

FIG. 21 is a top view of a multi-electrode array 100 according to various aspects of the present disclosure. The array 100 may be substantially similar to that disclosed with reference to FIGS. 1-20. In that regard, the array 100 includes a plurality of electrodes 102 arranged on a substrate 500. The array 100 may take the form of a non-rectangular arrangement of electrodes, such as the hexagonal configuration of the illustrated embodiment. It is recognized by one of ordinary skill in the art that the array 100 is not limited to any particular arrangement, and further configurations are both contemplated and provided for.

As disclosed with reference to FIGS. 1-20, electrode spacing may vary throughout the array 100. That is, a first electrode spacing may be different from or substantially similar to a second electrode spacing based on considerations including characteristics of the carrier medium and/or the respective target structures. Likewise, an electrode spacing in a first direction may be different from or substantially similar to an electrode spacing in a second direction based on similar considerations. In this way, the electrodes 102 can be adapted to a particular target-containing medium.

Figure 22:
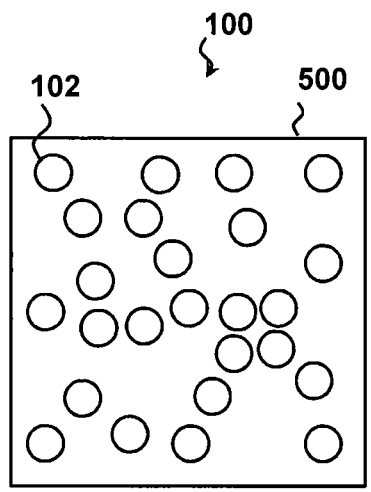

FIG. 22 is a top view of a multi-electrode array 100 according to various aspects of the present disclosure. The array 100 may be substantially similar to that disclosed with reference to FIGS. 1-21. In that regard, the array 100 includes a plurality of electrodes 102 arranged on a substrate 500. In the illustrated embodiment, the array 100 includes an irregular distribution of electrodes 102. The irregular distribution may be determined, in part, by a target-containing medium where the arrangement of each electrode 102 is configured to contact a particular target within the medium 112.

Figure 23:
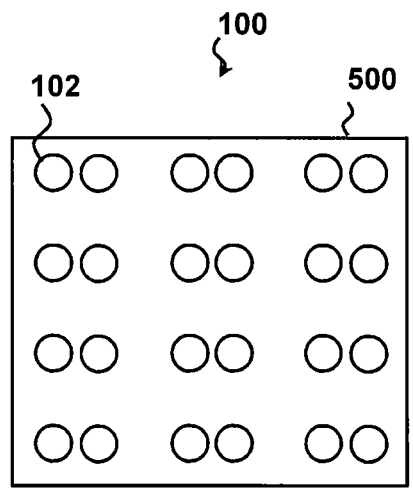

FIG. 23 is a top view of a multi-electrode array 100 according to various aspects of the present disclosure. The array 100 may be substantially similar to that disclosed with reference to FIGS. 1-22. In that regard, the array 100 includes a plurality of electrodes 102 arranged on a substrate 500. In the illustrated embodiment, the array 100 includes a symmetrical pairing of electrodes 102. This configuration may be referred to as an adjacent-return configuration. The pairing and the positioning of the electrode 102 pairs may be determined, in part, by a target-containing medium where the arrangement of each electrode 102 is configured to contact a particular target within the medium 112.

Figure 24:
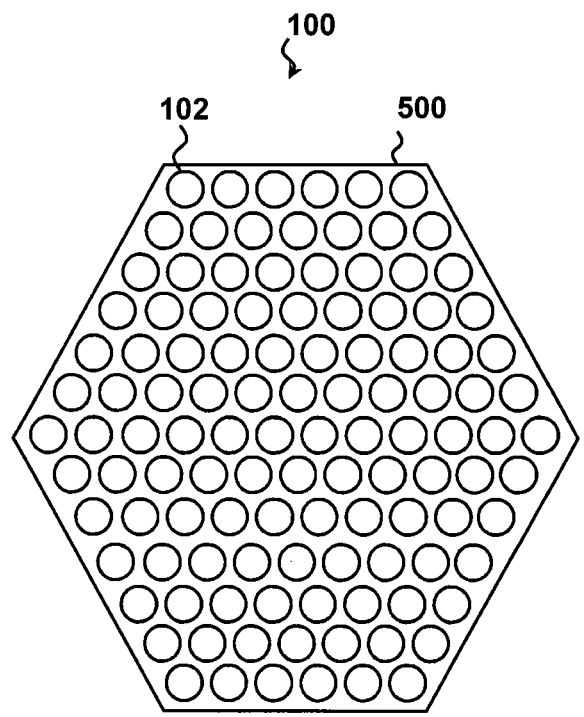

FIG. 24 is a top view of a multi-electrode array 100 according to various aspects of the present disclosure. The array 100 may be substantially similar to that disclosed with reference to FIGS. 1-23. In that regard, the array 100 includes a plurality of electrodes 102 arranged on a substrate 500. In the illustrated embodiment, the array 100 includes a hexagonal array of electrodes 102. The rows and columns of electrodes 102 are offset to increase electrode 102 density. The positioning of each individual electrode 102 may be determined, in part, by a target-containing medium where the arrangement of each electrode 102 is configured to contact a particular target within the medium 112. It is recognized by one of ordinary skill in the art that the preceding arrays are merely exemplary and are not limiting. Further configurations are both contemplated and provided for.

Figure 25:
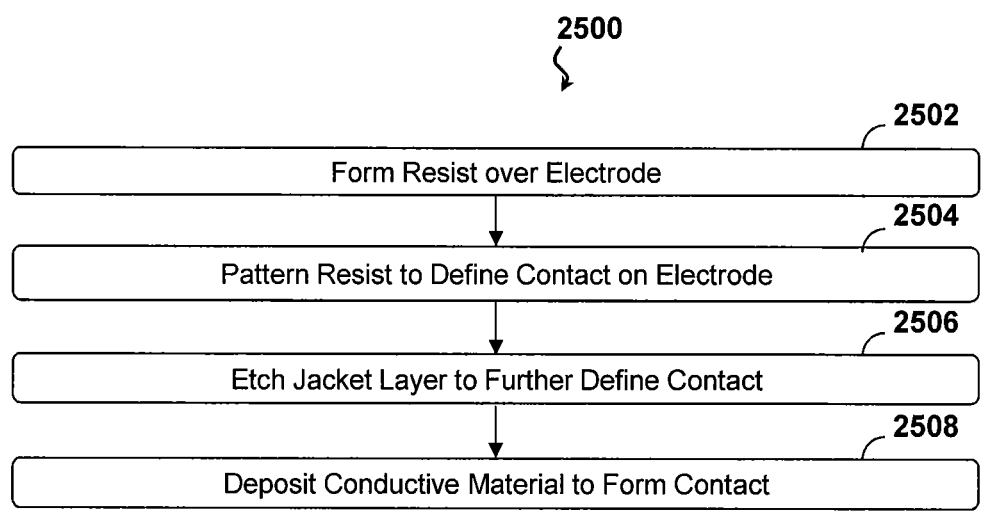
FIG. 25 is a flow diagram of a method for forming a conductive area along the body of an electrode according to various aspects of the present disclosure.

At any time during the fabrication of the array 100, additional contacts may be formed on one or more electrodes 102 of the array 100, such as the secondary conductive areas 132 of FIGS. 1A, 1B, 1C, and 1D. These additional contacts are coupled to the respective electrode cores 118, and, accordingly, the locations and shapes of the contacts may be individually tailored for each electrode 102 of the array 100 in order to electrically couple respective target structures 110 to the electrode cores 118. A method of forming these additional contacts is disclosed with reference to FIGS. 25-29. FIG. 25 is a flow diagram of a method 2500 for forming a conductive area along the body of an electrode 102 according to various aspects of the present disclosure. FIGS. 26-29 are diagrammatic cross-sectional views of an electrode 102 undergoing a method 2500 for forming a conductive area along the body of the electrode 102 according to various aspects of the present disclosure.

In the illustrated embodiments, an interface layer 106 has been formed on the electrode 102 at the tip end, and a jacket layer 108 has been formed along the body of the electrode. In that regard, the electrode 102 includes an interface layer 106, a jacket layer 108, and an electrode core 118 substantially similar to those disclosed with reference to FIGS. 1A, 1B, 1C, and 1D. In further embodiments, the interface layer 106 is formed at the tip end concurrent with the formation of the additional contacts.

Referring to block 2502 of FIG. 25 and to FIG. 26, a resist 2602 is formed over the electrode 102. The resist 2602 may be formed by any suitable process including spin-on deposition, spray deposition, PVD, CVD, HDP-CVD, ALD, ink-jet deposition, other suitable deposition processes, and/or combinations thereof. Referring to block 2504 of FIG. 25 and referring still to FIG. 26, the resist 2602 is patterned to define a cavity 2604 for the contact. In the case of ink-jet deposition, the deposition process may also pattern the resist 2602. In further embodiments, patterning of the resist 2602 includes soft baking, mask aligning, exposure, post-exposure baking, developing the photoresist, rinsing, drying (e.g., hard baking), and/or other suitable photolithographic steps. Any photolithographic steps may be performed using off-axis or tilt photolithography. Alternatively, the photolithographic process may be implemented, supplemented, or replaced by other methods such as maskless photolithography, electron-beam writing, and ion-beam writing.

Referring to block 2506 of FIG. 25 and to FIG. 27, the jacket layer 108 is patterned to expose the electrode core 118 and to further define the cavity 2604. Patterning may include any suitable removal processes including dry etching, wet etching, and/or other etching methods (e.g., reactive ion etching, etc.). Resist 2602 may be removed following the patterning of the jacket layer 108.

Referring to block 2508 of FIG. 25 and to FIGS. 28 and 29, in some embodiments, a conductive material 2802 is deposited within the cavity 2604 and coupled to the electrode core 118 via a metallization process. Metallization is not necessarily limited to the forming of purely metallic materials and may include depositing copper, aluminum, aluminum/silicon/copper alloy, titanium, titanium nitride, tungsten, nickel, polysilicon, metal silicide, other metallic and nonmetallic conductors such as PEDOT, and/or combinations thereof. Any suitable metallization process may be used. In one exemplary metallization process, a conductive material 2802 is deposited over the electrode 102 as illustrated in FIG. 28. Referring to FIG. 29, the conductive material 2802 is etched back, leaving conductive material 2802 within the cavity to form the contact (e.g., secondary conductive area 132).

Thus, the present disclosure provides a multi-electrode array configured for a target-containing carrier and a method for fabricating the array. The foregoing outlines features of several embodiments so that those of ordinary skill in the art may better understand the aspects of the present disclosure. In some embodiments, a multi-electrode array is provided. The array comprises: a substrate; and a plurality of electrodes disposed on the substrate, wherein each electrode of the plurality of electrodes has a conductive tip-end and an insulated remainder; wherein a first electrode of the plurality of electrodes has a first configuration selected to bring a conductive tip end of the first electrode in proximity to a first target structure; and wherein a second electrode of the plurality of electrodes has a second configuration selected to bring a conductive tip end of the second electrode in proximity to a second target structure, the first configuration and the second configuration being different.

In further embodiments, an electrical interface device is provided. The device comprises: a substrate having a front surface and a back surface opposite the front surface; a first electrode extending from the back surface, through the substrate, and to a height above the front surface, wherein the first electrode is electrically conductive throughout; and a second electrode extending from the back surface, through the substrate, and to a height above the front surface, wherein the second electrode is electrically conductive throughout, wherein the first electrode has a first configuration and the second electrode has a second configuration different from the first configuration.

In yet further embodiments, a method of fabricating an electrode array is provided. The method comprises: receiving a substrate having a front side and a backside; forming isolation features on the backside of the substrate; and performing a resist transfer process on the front side of the substrate, the resist transfer process being operable to form a plurality of electrodes on the front side of the substrate, wherein the resist transfer process is further operable to form a first electrode of the plurality of electrodes having a first configuration and a second electrode of the plurality of electrodes having a second configuration, wherein the first configuration and the second configuration are different, and wherein the first configuration and the second configuration are selected based on a target-containing carrier medium.

Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A method of forming an electrode array comprising:
   identifying structures in a tissue into which a plurality of electrodes are to be introduced;
   receiving a substrate having a plurality of conductive electrode regions defined thereupon;
   forming a resist on a top surface of the substrate; and
   using the resist to pattern the top surface the substrate, wherein the patterning defines a first electrode and a second electrode from the plurality of conductive electrode regions such that the first electrode has a different shape from the second electrode based on the identified structures in the tissue.

2. The method of claim 1, wherein the first electrode is different from the second electrode in at least one of: a height, a width, or a shape of a tip-end.

3. The method of claim 1 further comprising:
patterning a back surface of the substrate prior to the forming of the resist;
forming an isolation structure in the patterned back surface of the substrate, wherein the isolation structure electrically isolates the first electrode from the second electrode after the patterning of the front surface of the substrate.

4. The method of claim 1 further comprising:
forming a dielectric material on a back surface of the substrate;
patterning the dielectric material to expose a backside of the first electrode and the second electrode; and
forming a conductor within the patterned dielectric material such that a first portion of the conductor is electrically coupled to the first electrode and a second portion of the conductor is electrically coupled to the second electrode.

5. The method of claim 1 further comprising:
forming a biocompatible insulator on the first electrode and the second electrode.

6. The method of claim 5 further comprising:
forming a protective material between the first electrode and the second electrode, wherein the protective material exposes a tip-portion of the first electrode and a tip-portion of the second electrode;
removing the biocompatible insulator from the tip-portion of the first electrode and from the tip-portion of the second electrode; and
thereafter, forming a biocompatible conductor on the tip-portion of the first electrode and on the tip-portion of the second electrode.

7. A method of fabricating an electrode array, the method comprising:
receiving a substrate having a front side and a backside;
forming isolation features on the backside of the substrate; and
performing a resist transfer process on the front side of the substrate, the resist transfer process being operable to form a plurality of electrodes on the front side of the substrate,
wherein the resist transfer process is further operable to form a first electrode of the plurality of electrodes having a first configuration and a second electrode of the plurality of electrodes having a second configuration,
wherein the first configuration and the second configuration are different such that a conductive region of the first electrode is different from a conductive region of the second electrode in at least one of: a height, a width, or a shape of a tip-end, and
wherein the first configuration and the second configuration are selected based on a target-containing carrier medium.

8. The method of claim 7, wherein the isolation features electrically isolate the first electrode from the second electrode.

9. The method of claim 7 further comprising forming a first bonding pad and a second bonding pad on the backside of the substrate, wherein the first bonding pad is electrically coupled to the first electrode and the second bonding pad is electrically coupled to the second electrode.

10. The method of claim 7, wherein the resist transfer process includes:
forming a first resist material on the front side of the substrate;
lithographically patterning the first resist material;
patterning a first portion of the front side of the substrate using the patterned first resist material;
thereafter, forming a second resist material on the front side of the substrate;
lithographically patterning the second resist material; and
patterning a second portion of the front side of the substrate using the patterned second resist material.

11. The method of claim 10, wherein the patterning of the first portion forms the first electrode and the patterning of the second portion forms the second electrode.

12. The method of claim 7, wherein the first configuration and the second configuration are further different such that the conductive region of the first electrode has a different amount of a conductive interface layer disposed thereupon than the conductive region of the second electrode.

13. The method of claim 12, wherein the conductive interface layer includes a biocompatible material configured to reduce an electrical impedance between a target region and an electrode core material of the plurality of electrodes.

14. A method of fabrication comprising:
receiving a substrate having a conductive region;
patterning a front side of the substrate, wherein the patterning patterns the conductive region to define an electrode;
forming an insulating material on a first portion and a second portion of the patterned conductive region;
forming a resist surrounding the insulating material on the first portion of the patterned conductive region and exposing the insulating material on the second portion of the patterned conductive region;
selectively removing the insulating material from the first portion of the patterned conductive region using the resist; and
thereafter, forming an interface layer on the first portion of the patterned conductive region,
wherein the conductive region is a first conductive region,
wherein the electrode is a first electrode,
wherein the substrate further includes a second conductive region,
wherein the patterning further includes patterning the second conductive region to define a second electrode,
wherein the patterning is configured such that the second conductive region has a different shape from the first conductive region after the patterning, and
wherein the second conductive region is different from the first conductive region in at least one of: a height, a width, or a shape of a tip-end.

15. The method of claim 14, wherein the insulating material is a first insulating material, the method further comprising:
patterning a back side of the substrate prior to the patterning of the front side of the substrate in order to form a cavity in the back side of the substrate;
forming a second insulating material within the cavity such that the second insulating material electrically isolates the conductive region from a remainder of the substrate after the patterning of the front side of the substrate.

16. The method of claim 15, wherein the patterning of the front side of the substrate exposes the second insulating material.

17. The method of claim 14 further comprising:
forming a dielectric material on a back side of the substrate; and forming a conductive interconnect within the dielectric material, wherein the conductive interconnect is electrically coupled to the conductive region.

18. The method of claim 14, wherein the interface layer includes a biocompatible conductor.

19. The method of claim 18, wherein the insulating material includes a biocompatible material.

20. A method of fabrication comprising:
receiving a substrate having a conductive region;
patterning a front side of the substrate, wherein the patterning patterns the conductive region to define an electrode;
forming an insulating material on a first portion and a second portion of the patterned conductive region;
forming a resist surrounding the insulating material on the first portion of the patterned conductive region and exposing the insulating material on the second portion of the patterned conductive region;
selectively removing the insulating material from the first portion of the patterned conductive region using the resist; and
thereafter, forming an interface layer on the first portion of the patterned conductive region,
wherein the conductive region is a first conductive region,
wherein the electrode is a first electrode,
wherein the substrate further includes a second conductive region,
wherein the patterning further includes patterning the second conductive region to define a second electrode,
wherein the patterning is configured such that the second conductive region has a different shape from the first conductive region after the patterning, and
wherein the second conductive region has a different amount of the interface layer disposed thereupon than the first conductive region.

* * * * *